US012780901B2

(12) United States Patent
Kim et al.

(10) Patent No.: US 12,780,901 B2
(45) Date of Patent: Nov. 3, 2026

(54) TRIPLE AGONIST HAVING ACTIVITIES ON ALL OF GLUCAGON, GLP-1, AND GIP RECEPTORS AND USE THEREOF

(71) Applicant: HANMI PHARM. CO., LTD., Hwaseong-si (KR)

(72) Inventors: Jung Kuk Kim, Hwaseong-si (KR); Jong Suk Lee, Hwaseong-si (KR); Euh Lim Oh, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 717 days.

(21) Appl. No.: 18/250,150

(22) PCT Filed: Dec. 24, 2021

(86) PCT No.: PCT/KR2021/019791
§ 371 (c)(1),
(2) Date: Apr. 21, 2023

(87) PCT Pub. No.: WO2022/139538
PCT Pub. Date: Jun. 30, 2022

(65) Prior Publication Data

US 2023/0382974 A1 Nov. 30, 2023

(30) Foreign Application Priority Data

Dec. 24, 2020 (KR) ........................ 10-2020-0183576

(51) Int. Cl.
*C07K 14/72* (2006.01)
*A61K 38/00* (2006.01)
*A61K 47/68* (2017.01)

(52) U.S. Cl.
CPC .......... *C07K 14/72* (2013.01); *A61K 47/6811* (2017.08); *A61K 38/00* (2013.01); *C07K 2319/30* (2013.01)

(58) Field of Classification Search
CPC ...................................................... A61K 38/00
See application file for complete search history.

(56) References Cited

FOREIGN PATENT DOCUMENTS

| | | | |
|---|---|---|---|
| KR | 10-2016-0074008 | A | 6/2016 |
| KR | 10-2019-0060749 | A | 6/2019 |
| KR | 10-2020-0078413 | A | 7/2020 |
| WO | 2014049610 | A2 | 4/2014 |
| WO | 2017116204 | A1 | 7/2017 |
| WO | 2017116205 | A1 | 7/2017 |
| WO | 2020/214013 | A1 | 10/2020 |

OTHER PUBLICATIONS

Authier and Desbuquois, Cellular and Molecular Life Sciences, 2008, vol. 65, pp. 1880-1899 (Year: 2008).*
Chow et al, Chemical Review, 2019, vol. 119, pp. 9971-10001 (Year: 2019).*
Legre et al Advanced Therapetuics, 2018, vol. 1, article 1800052, 22 pages (Year: 2018).*
Lundquist and Pelletier, Organic Letters, 2002, vol. 4, pp. 3219-3221 (Year: 2002).*
Finan et al., "A rationally designed monomeric peptide triagonist corrects obesity and diabetes in rodents", Nature Medicine, vol. 21, No. 1, Jan. 2015, pp. 27-36 (13 pages).
Brandt et al., "Gut hormone polyagonists for the treatment of type 2 diabetes", Peptides, vol. 100, 2018, pp. 190-201.
Choi et al., "Potent body weight loss, and therapeutic efficacy in a NASH animal model by a novel long-acting GLP-1/GIP/Glucagon tri-agonist (HM15211)", Hanmi Pharm. Co., Ltd., 2017, 25 pages.
Extended European Search Report dated Oct. 24, 2024, in application No. 21911603.5.
Jonathan W Day et al., "A new glucagon and GLP-1 co-agonist eliminates obesity in rodents", Nature Chemical Biology, Oct. 2009, pp. 749-757, vol. 5, No. 10.

* cited by examiner

*Primary Examiner* — Karen A. Canella
(74) *Attorney, Agent, or Firm* — Sughrue Mion, PLLC

(57) ABSTRACT

Provided are a triple agonist having activities on all of glucagon, GLP-1, and GIP receptors, and use thereof.

20 Claims, No Drawings

Specification includes a Sequence Listing.

SEQUENCE LISTING

```
<160> NUMBER OF SEQ ID NOS: 36

<210> SEQ ID NO 1
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a
      lactam ring

<400> SEQUENCE: 1

Tyr Xaa Gln Gly Thr Phe Thr Ser Asp Tyr Ser Lys Tyr Leu Asp Glu
1               5                   10                  15

Gln Arg Ala Lys Glu Phe Val Gln Trp Leu Leu Asp His His Pro Ser
            20                  25                  30

Ser Gly Gln Pro Pro Pro Ser Cys
        35                  40


<210> SEQ ID NO 2
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a
      lactam ring

<400> SEQUENCE: 2

Tyr Xaa Gln Gly Thr Phe Thr Ser Asp Tyr Ser Lys Tyr Leu Asp Glu
1               5                   10                  15

Gln Ala Ala Lys Glu Phe Val Gln Trp Leu Leu Asp His His Pro Ser
            20                  25                  30

Ser Gly Gln Pro Pro Pro Ser Cys
        35                  40


<210> SEQ ID NO 3
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a
      lactam ring

<400> SEQUENCE: 3

Tyr Xaa Gln Gly Thr Phe Thr Ser Asp Tyr Ser Lys Tyr Leu Asp Glu
1               5                   10                  15
```

-continued

```
Gln Arg Ala Lys Glu Phe Ile Ala Trp Leu Leu Asp His His Pro Ser
            20                  25                  30

Ser Gly Gln Pro Pro Pro Ser Cys
        35                  40


<210> SEQ ID NO 4
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a
      lactam ring

<400> SEQUENCE: 4

Tyr Xaa Gln Gly Thr Phe Thr Ser Asp Tyr Ser Ile Tyr Leu Asp Glu
1               5                   10                  15

Gln Arg Ala Lys Glu Phe Ile Ala Trp Leu Leu Ala His His Pro Ser
            20                  25                  30

Ser Gly Gln Pro Pro Pro Ser Cys
        35                  40


<210> SEQ ID NO 5
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a
      lactam ring

<400> SEQUENCE: 5

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp Gln His Pro Ser
            20                  25                  30

Ser Gly Gln Pro Pro Pro Ser Cys
        35                  40


<210> SEQ ID NO 6
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a
      lactam ring
```

<400> SEQUENCE: 6

Tyr Xaa Gln Gly Thr Phe Thr Ser Asp Tyr Ser Lys Ala Leu Asp Glu
1               5                   10                  15

Lys Ala Ala Lys Asp Phe Val Gln Trp Leu Leu Asp Gln His Pro Ser
            20                  25                  30

Ser Gly Gln Pro Pro Pro Ser Cys
        35                  40

<210> SEQ ID NO 7
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a lactam ring

<400> SEQUENCE: 7

Tyr Xaa Gln Gly Thr Phe Thr Ser Asp Tyr Ser Lys Ala Leu Asp Glu
1               5                   10                  15

Lys Ala Ala Lys Asp Phe Val Gln Trp Leu Lys Asp Gln His Pro Ser
            20                  25                  30

Ser Gly Gln Pro Pro Pro Ser Cys
        35                  40

<210> SEQ ID NO 8
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a lactam ring

<400> SEQUENCE: 8

Tyr Xaa Gln Gly Thr Phe Thr Ser Asp Cys Ser Lys Tyr Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<220> FEATURE:
<221> NAME/KEY: MISC_FEATURE
<222> LOCATION: (12)..(16)
<223> OTHER INFORMATION: amino acids at positions 12 and 16 form a lactam ring

<400> SEQUENCE: 9

Tyr Xaa Glu Gly Thr Phe Thr Ser Asp Tyr Ser Glu Tyr Met Glu Lys
1 5 10 15

Glu Ala Val Arg Glu Phe Ile Cys Trp Leu Val Lys Gly Gly Pro Ser
20 25 30

Ser Gly Ala Pro Pro Pro Ser
35

<210> SEQ ID NO 10
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a lactam ring

<400> SEQUENCE: 10

Tyr Xaa Gln Gly Thr Phe Thr Ser Asp Tyr Ser Lys Tyr Leu Asp Glu
1 5 10 15

Arg Ala Ser Lys Asp Phe Val Gln Trp Leu Leu Asp His His Pro Ser
20 25 30

Ser Gly Gln Pro Pro Pro Ser Cys
35 40

<210> SEQ ID NO 11
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a lactam ring

<400> SEQUENCE: 11

Tyr Xaa Gln Gly Thr Phe Thr Ser Asp Tyr Ser Ile Tyr Leu Asp Glu
1 5 10 15

Lys Ala Ala Lys Glu Phe Val Gln Trp Leu Leu Asp Gln His Pro Ser
20 25 30

Ser Gly Gln Pro Pro Pro Ser Cys
35 40

<210> SEQ ID NO 12
<211> LENGTH: 40
<212> TYPE: PRT
<213> ORGANISM: Artificial Sequence
<220> FEATURE:

-continued

<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (20)
<223> OTHER INFORMATION: Xaa is aminoisobutyric acid (Aib)

<400> SEQUENCE: 12

```
Tyr Xaa Glu Gly Thr Phe Thr Ser Asp Tyr Ser Ile Gln Leu Asp Lys
1               5                   10                  15

Gln Ala Ala Xaa Ala Phe Val Gln Trp Leu Ile Ala Gly Gly Pro Ser
            20                  25                  30

Ser Gly Ala Pro Pro Pro Ser Lys
        35                  40
```

<210> SEQ ID NO 13
<211> LENGTH: 12
<212> TYPE: PRT
<213> ORGANISM: Homo sapiens

<400> SEQUENCE: 13

```
Glu Ser Lys Tyr Gly Pro Pro Cys Pro Ser Cys Pro
1               5                   10
```

<210> SEQ ID NO 14
<211> LENGTH: 11
<212> TYPE: PRT
<213> ORGANISM: Artificial Sequence
<220> FEATURE:
<223> OTHER INFORMATION: Variant of hinge region

<400> SEQUENCE: 14

```
Glu Ser Lys Tyr Gly Pro Pro Pro Ser Cys Pro
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: Variant of hinge region

<400> SEQUENCE: 15

```
Glu Ser Lys Tyr Gly Pro Pro Cys Pro Ser Pro
1               5                   10
```

<210> SEQ ID NO 16
<211> LENGTH: 10
<212> TYPE: PRT
<213> ORGANISM: Artificial Sequence
<220> FEATURE:
<223> OTHER INFORMATION: Variant of hinge region

<400> SEQUENCE: 16

```
Glu Ser Lys Tyr Gly Pro Pro Cys Pro Ser
1               5                   10
```

<210> SEQ ID NO 17
<211> LENGTH: 10
<212> TYPE: PRT
<213> ORGANISM: Artificial Sequence
<220> FEATURE:
<223> OTHER INFORMATION: Variant of hinge region

<400> SEQUENCE: 17

Glu Ser Lys Tyr Gly Pro Pro Cys Pro Pro
1 5 10

<210> SEQ ID NO 18
<211> LENGTH: 8
<212> TYPE: PRT
<213> ORGANISM: Artificial Sequence
<220> FEATURE:
<223> OTHER INFORMATION: Variant of hinge region

<400> SEQUENCE: 18

Lys Tyr Gly Pro Pro Cys Pro Ser
1 5

<210> SEQ ID NO 19
<211> LENGTH: 8
<212> TYPE: PRT
<213> ORGANISM: Artificial Sequence
<220> FEATURE:
<223> OTHER INFORMATION: Variant of hinge region

<400> SEQUENCE: 19

Glu Ser Lys Tyr Gly Pro Pro Cys
1 5

<210> SEQ ID NO 20
<211> LENGTH: 7
<212> TYPE: PRT
<213> ORGANISM: Artificial Sequence
<220> FEATURE:
<223> OTHER INFORMATION: Variant of hinge region

<400> SEQUENCE: 20

Glu Lys Tyr Gly Pro Pro Cys
1 5

<210> SEQ ID NO 21
<211> LENGTH: 6
<212> TYPE: PRT
<213> ORGANISM: Artificial Sequence
<220> FEATURE:
<223> OTHER INFORMATION: Variant of hinge region

<400> SEQUENCE: 21

Glu Ser Pro Ser Cys Pro
1 5

<210> SEQ ID NO 22
<211> LENGTH: 5
<212> TYPE: PRT
<213> ORGANISM: Artificial Sequence
<220> FEATURE:
<223> OTHER INFORMATION: Variant of hinge region

<400> SEQUENCE: 22

Glu Pro Ser Cys Pro
1 5

<210> SEQ ID NO 23
<211> LENGTH: 4
<212> TYPE: PRT
<213> ORGANISM: Artificial Sequence
<220> FEATURE:
<223> OTHER INFORMATION: Variant of hinge region

<400> SEQUENCE: 23

Pro Ser Cys Pro
1

<210> SEQ ID NO 24
<211> LENGTH: 10
<212> TYPE: PRT
<213> ORGANISM: Artificial Sequence
<220> FEATURE:
<223> OTHER INFORMATION: Variant of hinge region

<400> SEQUENCE: 24

Glu Ser Lys Tyr Gly Pro Pro Ser Cys Pro
1 5 10

<210> SEQ ID NO 25
<211> LENGTH: 9
<212> TYPE: PRT
<213> ORGANISM: Artificial Sequence
<220> FEATURE:
<223> OTHER INFORMATION: Variant of hinge region

<400> SEQUENCE: 25

Lys Tyr Gly Pro Pro Pro Ser Cys Pro
1 5

<210> SEQ ID NO 26
<211> LENGTH: 9
<212> TYPE: PRT
<213> ORGANISM: Artificial Sequence
<220> FEATURE:
<223> OTHER INFORMATION: Variant of hinge region

<400> SEQUENCE: 26

Glu Ser Lys Tyr Gly Pro Ser Cys Pro
1 5

<210> SEQ ID NO 27
<211> LENGTH: 8
<212> TYPE: PRT
<213> ORGANISM: Artificial Sequence
<220> FEATURE:
<223> OTHER INFORMATION: Variant of hinge region

<400> SEQUENCE: 27

Glu Ser Lys Tyr Gly Pro Pro Cys
1 5

<210> SEQ ID NO 28
<211> LENGTH: 7
<212> TYPE: PRT
<213> ORGANISM: Artificial Sequence
<220> FEATURE:
<223> OTHER INFORMATION: Variant of hinge region

<400> SEQUENCE: 28

Lys Tyr Gly Pro Pro Cys Pro
1 5

<210> SEQ ID NO 29
<211> LENGTH: 7
<212> TYPE: PRT
<213> ORGANISM: Artificial Sequence
<220> FEATURE:
<223> OTHER INFORMATION: Variant of hinge region

<400> SEQUENCE: 29

```
Glu Ser Lys Pro Ser Cys Pro
1               5


<210> SEQ ID NO 30
<211> LENGTH: 6
<212> TYPE: PRT
<213> ORGANISM: Artificial Sequence
<220> FEATURE:
<223> OTHER INFORMATION: Variant of hinge region

<400> SEQUENCE: 30

Glu Ser Pro Ser Cys Pro
1               5


<210> SEQ ID NO 31
<211> LENGTH: 4
<212> TYPE: PRT
<213> ORGANISM: Artificial Sequence
<220> FEATURE:
<223> OTHER INFORMATION: Variant of hinge region

<400> SEQUENCE: 31

Glu Pro Ser Cys
1


<210> SEQ ID NO 32
<211> LENGTH: 3
<212> TYPE: PRT
<213> ORGANISM: Artificial Sequence
<220> FEATURE:
<223> OTHER INFORMATION: Variant of hinge region

<400> SEQUENCE: 32

Ser Cys Pro
1


<210> SEQ ID NO 33
<211> LENGTH: 221
<212> TYPE: PRT
<213> ORGANISM: Homo sapiens

<400> SEQUENCE: 33

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160
```

Pro Glu Asn Asn Tyr Lys Thr Thr Pro Pro Val Leu Asp Ser Asp Gly
165 170 175

Ser Phe Phe Leu Tyr Ser Arg Leu Thr Val Asp Lys Ser Arg Trp Gln
180 185 190

Glu Gly Asn Val Phe Ser Cys Ser Val Met His Glu Ala Leu His Asn
195 200 205

His Tyr Thr Gln Lys Ser Leu Ser Leu Ser Leu Gly Lys
210 215 220

<210> SEQ ID NO 34
<211> LENGTH: 442
<212> TYPE: PRT
<213> ORGANISM: Homo sapiens
<220> FEATURE:
<221> NAME/KEY: MISC_FEATURE
<222> LOCATION: (1)..(442)
<223> OTHER INFORMATION: Amino acids at position 1 to 442 form Human Immunoglobulin G4 Fc Fragment (homodimer)
<220> FEATURE:
<221> NAME/KEY: MISC_FEATURE
<222> LOCATION: (1)..(221)
<223> OTHER INFORMATION: Amino acids at position 1 to 221 form one monomer
<220> FEATURE:
<221> NAME/KEY: MISC_FEATURE
<222> LOCATION: (222)..(442)
<223> OTHER INFORMATION: Amino acids at position 222 to 442 form one monomer
<220> FEATURE:
<221> NAME/KEY: DISULFID
<222> LOCATION: (3)..(224)
<223> OTHER INFORMATION: Amino acids at position 3 and position 224 form an inter-disulfide bond
<220> FEATURE:
<221> NAME/KEY: DISULFID
<222> LOCATION: (35)..(95)
<223> OTHER INFORMATION: Amino acids at position 35 and position 95 form an intra-chain disulfide bond
<220> FEATURE:
<221> NAME/KEY: DISULFID
<222> LOCATION: (141)..(199)
<223> OTHER INFORMATION: Amino acids at position 141 and position 199 form an intra-chain disulfide bond
<220> FEATURE:
<221> NAME/KEY: DISULFID
<222> LOCATION: (256)..(316)
<223> OTHER INFORMATION: Amino acids at position 256 and position 316 form an intra-chain disulfide bond
<220> FEATURE:
<221> NAME/KEY: DISULFID
<222> LOCATION: (362)..(420)
<223> OTHER INFORMATION: Amino acids at position 362 and position 420 form an intra-chain disulfide bond

<400> SEQUENCE: 34

Pro Ser Cys Pro Ala Pro Glu Phe Leu Gly Gly Pro Ser Val Phe Leu
1 5 10 15

Phe Pro Pro Lys Pro Lys Asp Thr Leu Met Ile Ser Arg Thr Pro Glu
20 25 30

Val Thr Cys Val Val Val Asp Val Ser Gln Glu Asp Pro Glu Val Gln
35 40 45

Phe Asn Trp Tyr Val Asp Gly Val Glu Val His Asn Ala Lys Thr Lys
50 55 60

Pro Arg Glu Glu Gln Phe Asn Ser Thr Tyr Arg Val Val Ser Val Leu
65 70 75 80

Thr Val Leu His Gln Asp Trp Leu Asn Gly Lys Glu Tyr Lys Cys Lys
85 90 95

```
Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440


<210> SEQ ID NO 35
<211> LENGTH: 4
<212> TYPE: PRT
<213> ORGANISM: Artificial Sequence
<220> FEATURE:
<223> OTHER INFORMATION: partial sequecne of the trigonal agonist
      (X27-X30)

<400> SEQUENCE: 35

Leu Asp His His
1
```

-continued

```
<210> SEQ ID NO 36
<211> LENGTH: 4
<212> TYPE: PRT
<213> ORGANISM: Artificial Sequence
<220> FEATURE:
<223> OTHER INFORMATION: partial sequecne of the trigonal agonist
      (X27-X30)

<400> SEQUENCE: 36

Leu Asp Gln His
1
```

TRIPLE AGONIST HAVING ACTIVITIES ON ALL OF GLUCAGON, GLP-1, AND GIP RECEPTORS AND USE THEREOF

CROSS REFERENCE TO RELATED APPLICATIONS

This Application is a National Stage of International Application No. PCT/KR2021/019791 filed Dec. 24, 2021, claiming priority based on Korean Patent Application No. 10-2020-0183576 filed Dec. 24, 2020.

INCORPORATION BY REFERENCE OF SEQUENCE LISTING

The content of the electronically submitted sequence listing, file name: Q287074SubstituteSEQLIST-ST25.txt; size: 19,010 bytes; and date of creation: May 30, 2026, filed herewith, is incorporated herein by reference in its entirety.

TECHNICAL FIELD

The present invention relates to a triple agonist having activities on all of glucagon, GLP-1, and GIP receptors, and use thereof.

BACKGROUND ART

Glucagon-like peptide-1 (GLP-1) and glucose-dependent insulinotropic polypeptide (GIP) are representative gastrointestinal hormones and neuronal hormones, and are materials involved in the control of blood glucose levels according to food intake. Glucagon, which is a peptide hormone secreted from the pancreas, is involved in controlling blood glucose levels along with the two materials described above.

GLP-1, which is a hormone secreted from the small intestine when stimulated by food intake, promotes insulin secretion of the pancreas in a blood glucose-dependent manner, and suppresses the secretion of glucagon to help lower blood glucose levels. In addition, GLP-1 acts as a satiety factor to slow digestion in the stomach and to delay the transit time of the digested food, thereby reducing food intake. Moreover, it has been reported that when administered to mice, GLP-1 has effects of food intake suppression and weight loss, and it was confirmed that these effects are observed both in normal and obese states, demonstrating its potential as a therapeutic agent for obesity.

Along with GLP-1, GIP, which is one of the gastrointestinal hormones secreted when stimulated by food intake, is a hormone composed of 42 amino acids secreted from K cells in the small intestine. GIP functions to promote insulin secretion from the pancreas in a blood glucose-dependent manner and helps lower blood glucose levels. Its effect of increasing GLP-1 activity has been reported.

Glucagon is produced in the pancreas when blood glucose begins to drop due to drug treatment, disease, or hormone or enzyme deficiency. Glucagon signals the liver to break down glycogen to induce the release of glucose, and has a role in increasing blood glucose to normal levels. In addition to the effect of increasing blood glucose levels, glucagon has been reported to exhibit anti-obesity effects by suppressing appetite in animals and humans, activating hormone-sensitive lipase in adipocytes to promote fat breakdown and energy expenditure.

In addition, studies have been conducted on a dual agonist having activities both on GLP-1 receptor and glucagon receptor as an alternative to the above-described GLP-1-based therapeutic substances and for maximizing the weight loss effect. It has been reported that the dual agonist has a superior weight loss effect, as compared to the existing treatment of GLP-1 alone, due to the activity on the glucagon receptor (Jonathan W et al., *Nat Chem Bio.,* 2009 October (5); 749-757).

In addition, in recent studies on a triple agonist (or triple agonist) that simultaneously acts on all of GLP-1, GIP, and glucagon receptors, efforts have been made to increase the half-life through modifications such as substitution of amino acid sequences to increase resistance to dipeptidyl peptidase-IV (DPP-IV), which degrades gastrointestinal hormones to cause loss of activity thereof. However, the effect of activating the three different receptors was not high, and triple agonists with various activity ratios were not shown. Accordingly, there is an increasing demand for a novel substance capable of highly activating GLP-1, GIP, and glucagon receptors.

There is also an increasing demand for the development of substances with various activity ratios for GLP-1, GIP, and glucagon receptors. For example, it is necessary to develop a substance which has high GLP-1 and GIP activities for enhancement of blood glucose control while having a relatively low glucagon activity, thereby exhibiting a blood glucose control effect that is higher than the weight loss effect, or a substance which has high GLP-1, GIP, and glucagon activities at the same time, thereby exhibiting the high weight loss effect.

Meanwhile, in recent years, there have been many changes in dietary habits, along with economic growth and changes in lifestyle. In particular, overweight and obesity are increasing due to Western-style dietary patterns. Overweight and obesity increase blood pressure and cholesterol levels, which causes the onset or exacerbation of various diseases such as heart disease, diabetes, arthritis, etc. Overweight and obesity are also major factors that increase the incidence of arteriosclerosis, hypertension, hyperlipidemia, or heart disease in children and adolescents as well as in adults.

As described, obesity is a worldwide disease and is a serious disease that causes various diseases. Nevertheless, treatment of obesity is not easy, because obesity is a complex disease involving a mechanism of action related to appetite control and energy metabolism. Therefore, treatment of obesity requires not only patients' own effort but also a method of treating an abnormal mechanism of action related to appetite control and energy metabolism. Accordingly, it is necessary to develop a drug capable of treating the abnormal mechanism of action.

For example, efforts have been continued in order to develop a substance having activities on GLP-1, GIP, and glucagon receptors as a therapeutic agent for the treatment of obesity and related metabolic syndrome.

DISCLOSURE

Technical Problem

There is a need to develop substances with varying rates of activation to GLP-1, GIP, and glucagon receptors.

Technical Solution

An object of the present invention is to provide a peptide having activities on a glucagon receptor, a glucagon-like peptide-1 (GLP-1) receptor, and a glucose-dependent insulinotropic polypeptide (GIP) receptor.

Another object of the present invention is to provide a conjugate including the peptide.

Still another object of the present invention is to provide a polynucleotide encoding the peptide, a recombinant expression vector including the polynucleotide, and a transformant including the polynucleotide or the recombinant expression vector.

Still another object of the present invention is to provide a method of preparing the peptide.

Still another object of the present invention is to provide a pharmaceutical composition for preventing or treating metabolic syndrome, the pharmaceutical composition including the peptide or the conjugate.

Still another object of the present invention is to provide use of the peptide or the composition in the preparation of a drug.

Still another object of the present invention is to provide a method of preventing or treating metabolic syndrome, the method including the step of administering, to an individual, the peptide, the conjugate, or the composition including the same.

Advantageous Effects

A peptide according to the present invention has activities on a glucagon receptor, a glucagon-like peptide-1 (GLP-1) receptor, and a glucose-dependent insulinotropic polypeptide (GIP) receptor, and may be used as a therapeutic agent for metabolic syndrome.

BEST MODE FOR CARRYING OUT THE INVENTION

To achieve the above objects, an aspect of the present invention provides a peptide having activities on a glucagon receptor, a glucagon-like peptide-1 (GLP-1) receptor, and a glucose-dependent insulinotropic polypeptide (GIP) receptor.

In one specific embodiment, the peptide is characterized in that it is a peptide including any one sequence selected from the group consisting of SEQ ID NOS: 1 to 12.

In another specific embodiment, the peptide is characterized in that it has 3% or more activities on a GLP-1 receptor, a glucagon receptor, and a GIP receptor, as compared with activities of native human GLP-1, glucagon, and GIP.

The peptide according to any one of the specific embodiments is characterized in that it has 10% or more activities on a GLP-1 receptor, a glucagon receptor, and a GIP receptor, as compared with activities of native human GLP-1, glucagon, and GIP.

The peptide according to any one of the specific embodiments is characterized in that it has 70% or more activities on a GLP-1 receptor, a glucagon receptor, and a GIP receptor, as compared with activities of native human GLP-1, glucagon, and GIP.

The peptide according to any one of the specific embodiments is characterized in that it has 70% or more activity on a GLP-1 receptor, as compared with activity of native human GLP-1.

The peptide according to any one of the specific embodiments is characterized in that it has 70% or more activity on a glucagon receptor, as compared with activity of native human glucagon.

The peptide according to any one of the specific embodiments is characterized in that it has 70% or more activity on a GIP receptor, as compared with activity of native human GIP.

The peptide according to any one of the specific embodiments is characterized in that it has 100% or more activity on a glucagon receptor, as compared with activity of native glucagon while having 10% or more activities on both of a GLP-1 receptor and a GIP receptor, as compared with activities of native GLP-1 and GIP.

The peptide according to any one of the specific embodiments is characterized in that it has 100% or more activity on a GIP receptor, as compared with activity of native GIP while having 10% or more activities on both of a GLP-1 receptor and a glucagon receptor, as compared with activities of native GLP-1 and glucagon.

The peptide according to any one of the specific embodiments is characterized in that an amino acid at position 12 and an amino acid at position 16, or an amino acid at position 16 and an amino acid at position 20 from the N-terminus form a ring.

The peptide according to any one of the specific embodiments is characterized in that the C-terminus thereof is amidated.

The peptide according to any one of the specific embodiments is characterized in that it is in the form of a long-acting conjugate, in which a material capable of increasing the half-life of the peptide is linked.

Another aspect of the present invention provides a long-acting conjugate represented by the following Chemical Formula 1:

X-L-F [Chemical Formula 1]

wherein X represents a peptide having activities on a glucagon receptor, a glucagon-like peptide-1 (GLP-1) receptor, and a glucose-dependent insulinotropic polypeptide (GIP) receptor;

L represents a linker including ethylene glycol repeating units,

F represents an immunoglobulin Fc region, and

- represents a covalent linkage between X and L and between L and F.

In one specific embodiment, X is characterized in that it is a peptide including any one sequence selected from the group consisting of SEQ ID NOS: 1 to 12.

In another specific embodiment, the peptide is characterized in that it is amidated at the C-terminus thereof.

The conjugate according to any one of the specific embodiments is characterized in that the immunoglobulin Fc region is an immunoglobulin Fc region derived from IgG, IgA, IgD, IgE, or IgM.

The conjugate according to any one of the specific embodiments is characterized in that the immunoglobulin Fc region is an immunoglobulin Fc region derived from IgG, IgA, IgD, IgE, or IgM, or a combination thereof or a hybrid thereof.

The pharmaceutical composition according to any one of the specific embodiments is characterized in that the immunoglobulin Fc region is derived from an IgG Fc region.

The conjugate according to any one of the specific embodiments is characterized in that the immunoglobulin Fc region is an IgG4 Fc region.

The conjugate according to any one of the specific embodiments is characterized in that the immunoglobulin Fc region is aglycosylated.

The conjugate according to any one of the specific embodiments is characterized in that the immunoglobulin Fc region is an aglycosylated Fc region derived from human IgG4.

The conjugate according to any one of the specific embodiments is characterized in that the immunoglobulin Fc region is selected from the group consisting of (a) CH1 domain, CH2 domain, CH3 domain, and CH4 domain; (b) CH1 domain and CH2 domain; (c) CH1 domain and CH3 domain; (d) CH2 domain and CH3 domain; and (e) a combination between one or two or more domains among CH1 domain, CH2 domain, CH3 domain, and CH4 domain, and an immunoglobulin hinge region or a part of the hinge region.

The conjugate according to any one of the specific embodiments is characterized in that the immunoglobulin Fc region has a structure, in which two polypeptide chains are linked via disulfide bonds, wherein they are linked via only a nitrogen atom of one chain of the two chains.

The conjugate according to any one of the specific embodiments is characterized in that the immunoglobulin Fc region has a dimeric form.

The conjugate according to any one of the specific embodiments is characterized in that the immunoglobulin Fc region includes a monomer having an amino acid sequence of SEQ ID NO: 33.

The conjugate according to any one of the specific embodiments is characterized in that the immunoglobulin Fc region is a homodimer of the monomer having the amino acid sequence of SEQ ID NO: 33.

The conjugate according to any one of the specific embodiments is characterized in that the immunoglobulin Fc region is linked via a nitrogen atom of proline at the N-terminus thereof.

The conjugate according to any one of the specific embodiments is characterized in that the immunoglobulin Fc region F and X are not glycosylated.

The conjugate according to any one of the specific embodiments is characterized in that L is a linker including ethylene glycol repeating units.

The conjugate according to any one of the specific embodiments is characterized in that the ethylene glycol repeating unit is represented by $[OCH_2CH_2]_n$, wherein n is a natural number, which is determined such that an average molecular weight, e.g., a number average molecular weight of $[OCH_2CH_2]_n$ in the peptide conjugate is 1 kDa to 100 kDa.

The conjugate according to any one of the specific embodiments is characterized in that the value of n is determined such that an average molecular weight, e.g., a number average molecular weight of $[OCH_2CH_2]_n$ in the peptide conjugate is 10 kDa.

The conjugate according to any one of the specific embodiments is characterized in that a formula weight of the ethylene glycol repeating unit moiety in L is in the range of 1 kDa to 100 kDa.

The conjugate according to any one of the specific embodiments is characterized in that L is polyethylene glycol.

The conjugate according to any one of the specific embodiments is characterized in that L is a linker including ethylene glycol repeating units, and F is a dimeric immunoglobulin Fc region.

The conjugate according to any one of the specific embodiments is characterized in that one X molecule is covalently linked to one Fc region chain of the dimeric immunoglobulin Fc region via the linker including ethylene glycol repeating units.

The conjugate according to any one of the specific embodiments is characterized in that one end of the linker including the ethylene glycol repeating units is linked to only one Fc region chain of the two Fc region chains of the dimeric immunoglobulin Fc region. The conjugate according to any one of the specific embodiments is characterized in that F and X are linked to each other via covalent bonds formed by reacting one end of L with an amine group or a thiol group of F and by reacting the other end of L with an amine group or a thiol group of X, respectively.

Still another aspect of the present invention provides a polynucleotide encoding the peptide, a recombinant expression vector including the polynucleotide, and a transformant including the polynucleotide or the recombinant expression vector.

Still another aspect of the present invention provides a method of preparing the peptide or the conjugate.

Still another aspect of the present invention provides a composition including the peptide or the conjugate.

In one specific embodiment, the composition is characterized in that it is a pharmaceutical composition for preventing or treating metabolic syndrome.

In another specific embodiment, the peptide is characterized by including any one sequence selected from the group consisting of SEQ ID NOS: 1 to 12.

The composition according to any one of the specific embodiments is characterized in that the peptide is in the form of a long-acting conjugate, which is represented by the following Chemical Formula 1:

X-L-F [Chemical Formula 1]

wherein X represents the peptide;

L represents a linker including ethylene glycol repeating units,

F represents an immunoglobulin Fc region, and

- represents a covalent linkage between X and L and between L and F.

The composition according to any one of the specific embodiments is characterized in that the metabolic syndrome is one or more selected from the group consisting of impaired glucose tolerance, hypercholesterolemia, dyslipidemia, obesity, diabetes, hypertension, dyslipidemia-induced arteriosclerosis, atherosclerosis, arteriosclerosis, and coronary heart disease.

Still another aspect of the present invention provides a method of preventing or treating metabolic syndrome, the method including the step of administering the peptide, the conjugate of the peptide, or a composition including the same to an individual in need thereof.

Still another aspect of the present invention provides use of the peptide, the conjugate of the peptide, or the composition for the prevention or treatment of metabolic syndrome.

Still another aspect of the present invention provides use of the peptide, the conjugate of the peptide, or the composition in the preparation of a drug for the prevention or treatment of metabolic syndrome.

MODE FOR CARRYING OUT THE INVENTION

Hereinafter, the present invention will be described in more detail.

Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below. Furthermore, a number of papers and patent documents are referenced and cited throughout this specification. The disclosures of the cited papers and patent documents are incorporated herein by reference in their entirety to further clarify the level and scope of the subject matter to which the present invention pertains.

Throughout the entire specification, not only the common one-letter or three-letter codes for naturally occurring amino acids, but also those three-letter codes generally allowed for other amino acids are used, such as 2-aminoisobutyric acid (Aib), N-methylglycine (Sar), and α-methyl-glutamic acid, etc. Further, the amino acids mentioned in abbreviations herein are described according to the IUPAC-IUB rules as follows:

| | | | |
|---|---|---|---|
| Alanine | Ala, A | Arginine | Arg, R |
| Asparagine | Asn, N | Aspartic acid | Asp, D |
| Cysteine | Cys, C | Glutamic acid | Glu, E |
| Glutamine | Gln, Q | Glycine | Gly, G |
| Histidine | His, H | Isoleucine | Ile, I |
| Leucine | Leu, L | Lysine | Lys, K |
| Methionine | Met, M | Phenylalanine | Phe, F |
| Proline | Pro, P | Serine | Ser, S |
| Threonine | Thr, T | Tryptophan | Trp, W |
| Tyrosine | Tyr, Y | Valine | Val, V |

As used herein, "Aib" may be used interchangeably with "2-aminoisobutyric acid" or "aminoisobutyric acid", and 2-aminoisobutyric acid and aminoisobutyric acid may be used interchangeably with each other.

One aspect of the present invention provides a peptide having activities on a glucagon receptor, a glucagon-like peptide-1 (GLP-1) receptor, and a glucose-dependent insulinotropic polypeptide (GIP) receptor.

The peptide having activities on glucagon, GLP-1, and GIP receptors may be used interchangeably with a "peptide" or "triple agonist".

In one specific embodiment, the triple agonist may include an amino acid sequence selected from the group consisting of SEQ ID NOS: 1 to 12, may essentially consist of an amino acid sequence selected from the group consisting of SEQ ID NOS: 1 to 12, or may consist of an amino acid sequence selected from the group consisting of SEQ ID NOS: 1 to 12, but is not limited thereto.

In the present specification, although described as a peptide "consisting of" a specific sequence number, as long as the peptide may have an activity identical or corresponding to that of the peptide consisting of the amino acid sequence of the corresponding sequence number, addition of a meaningless sequence upstream or downstream of the amino acid sequence of the corresponding sequence number, a naturally occurring mutation, or a silent mutation therein is not excluded, and it will be apparent that those having such a sequence addition or mutation are also included in the scope of the present invention.

The triple agonist of the present invention may significantly activate one or more, two or more, or all of glucagon receptor, GLP-1 receptor, and GIP receptor, but is not limited thereto.

The triple agonist of the present invention is characterized by possessing one or more activities of the following i) to iii), specifically significant activities:

i) activation of GLP-1 receptor; ii) activation of glucagon receptor; and iii) activation of GIP receptor.

Here, the activation of the receptor may be exemplified by exhibiting 0.1% or more, 1% or more, 2% or more, 3% or more, 4% or more, 5% or more, 6% or more, 7% or more, 8% or more, 9% or more, 10% or more, 20% or more, 30% or more, 40% or more, 50% or more, 60% or more, 70% or more, 80% or more, 90% or more, 100% or more, 200% or more, 300% or more, 400% or more, 500% or more, 600% or more, 700% or more, 800% or more in vitro activity on the receptor, as compared with a native form thereof, but is not limited thereto.

The triple agonist having significant levels of activities on glucagon, GLP-1, and GIP receptors may exhibit, but is not particularly limited to, 0.1% or more, 1% or more, 2% or more, 3% or more, 4% or more, 5% or more, 6% or more, 7% or more, 8% or more, 9% or more, 10% or more, 20% or more, 30% or more, 40% or more, 50% or more, 60% or more, 70% or more, 80% or more, 90% or more, 100% or more, 200% or more, 300% or more, 400% or more, 500% or more, 600% or more, 700% or more, or 800% or more in vitro activity on one or more receptors, specifically two or more receptors, and more specifically all of the three receptors of glucagon, GLP-1, and GIP receptors, as compared with the native ligand (native glucagon, native GLP-1, and native GIP) of the corresponding receptor.

A method of measuring the in vitro activity of the triple agonist may be performed with reference to Example 3 of the present specification, but is not particularly limited thereto.

In one specific embodiment, the triple agonist of the present invention may have 3% or more activity on GLP-1, glucagon, and GIP receptors, as compared with native human GLP-1, glucagon, and GIP, but is not particularly limited thereto.

In another specific embodiment, the triple agonist of the present invention may have 10% or more activity on GLP-1, glucagon, and GIP receptors, as compared with native human GLP-1, glucagon, and GIP, but is not particularly limited thereto. The triple agonist may be exemplified by a peptide including any one amino acid sequence of SEQ ID NOS: 1 to 6, and SEQ ID NOS: 9 to 11, but is not limited thereto.

In still another specific embodiment, the triple agonist of the present invention may have 70% or more activity on GLP-1, glucagon, and GIP receptors, as compared with native human GLP-1, glucagon, and GIP, but is not particularly limited thereto. The triple agonist may be exemplified by a peptide including the amino acid sequence of SEQ ID NO: 2 or 6, but is not limited thereto.

In still another specific embodiment, the triple agonist of the present invention may have 70% or more activity on GLP-1 receptor, as compared with native human GLP-1. The triple agonist may be exemplified by a peptide including any one amino acid sequence of SEQ ID NOS: 2, 6, 7, 11, and 12, but is not limited thereto.

In still another specific embodiment, the triple agonist of the present invention may have 70% or more activity on glucagon receptor, as compared with native human glucagon. The triple agonist may be exemplified by a peptide including any one amino acid sequence of SEQ ID NOS: 1 to 3, 5, and 6, but is not limited thereto.

In still another specific embodiment, the triple agonist of the present invention may have 70% or more activity on GIP receptor, as compared with native human GIP. The triple agonist may be exemplified by a peptide including any one amino acid sequence of SEQ ID NOS: 1, 2, 4, and 6, but is not limited thereto.

The triple agonist of the present invention may exhibit significant activity, for example, 10% or more, 30% or more, 50% or more, or 70% or more activity on two or more receptors of GLP-1 receptor, glucagon receptor, and GIP receptor while exhibiting particularly excellent activity, for example, 100% or more, 150% or more, 200% or more, 300% or more, 400% or more, or 500% or more activity on the other receptor, but is not limited thereto.

In one specific embodiment, the triple agonist of the present invention may have 10% or more activity on both of GLP-1 receptor and GIP receptor, as compared with the native GLP-1 and GIP while having 100% or more activity on glucagon receptor, as compared with the native glucagon. The triple agonist of the present invention may be exemplified by a peptide including any one amino acid sequence of SEQ ID NOS: 1, 2, 3, and 5, but is not limited thereto.

In another specific embodiment, the triple agonist of the present invention may have 10% or more activity on both of GLP-1 receptor and glucagon receptor, as compared with the native GLP-1 and GIP while having 100% or more activity on GIP receptor, as compared with the native GIP. The triple agonist of the present invention may be exemplified by a peptide including any one amino acid sequence of SEQ ID NOS: 2, 4 and 6, but is not limited thereto.

In still another specific embodiment, the triple agonist of the present invention may include an amino acid sequence of SEQ ID NO: 35, but is not particularly limited thereto. The triple agonist may include the amino acid sequence of SEQ ID NO: 35 as residues at positions 27 to 30 from the N-terminus of the peptide, and may be exemplified by a peptide including any one amino acid sequence of SEQ ID NOS: 1 to 3, 8, and 10, but is not limited thereto.

In still another specific embodiment, the triple agonist of the present invention may include an amino acid sequence of SEQ ID NO: 36, but is not particularly limited thereto. The triple agonist may include the amino acid sequence of SEQ ID NO: 36 as residues at positions 27 to 30 from the N-terminus of the peptide, and may be exemplified by a peptide including any one amino acid sequence of SEQ ID NOS: 5, 6, and 11, but is not limited thereto.

Further, the triple agonist of the present invention may include an amino acid sequence having at least 70%, 75%, 80%, 85%, 90%, 95%, 96%, 97%, 98%, 99%, 99.5%, 99.7% or 99.9% or more homology or identity to the amino acid sequences of SEQ ID NOS: 1 to 12. Further, it is obvious that a peptide having an amino acid sequence with deletion, modification, substitution, conservative substitution, or addition in part of the sequence may also be included within the scope of the present disclosure, as long as the amino acid sequence has such homology or identity and exhibits efficacy corresponding to that of the triple agonist of the present invention.

For example, the peptide includes a peptide having sequence addition or deletion, naturally occurring mutation, silent mutation, or conservative substitution, which does not alter the function of the triple agonist of the present invention, at the N-terminus or C-terminus of the amino acid sequence, and/or inside thereof.

The "conservative substitution" means replacement of an amino acid with another amino acid having similar structural and/or chemical properties. This amino acid substitution may be generally made on the basis of similarity in polarity, charge, solubility, hydrophobicity, hydrophilicity, and/or amphipathic nature of residues. Commonly, the conservative substitution may rarely affect or may not affect activity of a protein or a peptide.

As used herein, the term "homology" or "identity" refers to the degree of relatedness between two given amino acid sequences or nucleotide sequences, and may be expressed as a percentage. The terms "homology" and "identity" may be often used interchangeably with each other.

The sequence homology or identity of conserved polynucleotides or polypeptides may be determined by standard alignment algorithms, and may be used together with a default gap penalty established by the program being used. Substantially, homologous or identical sequences are generally expected to hybridize to all or part of the sequences under moderate or high stringent conditions. It is apparent that hybridization also includes hybridization with polynucleotides containing general codons or codons in consideration of codon degeneracy in polynucleotides.

Whether any two polynucleotide or polypeptide sequences have homology, similarity, or identity may be determined by a known computer algorithm such as the "FASTA" program as in Pearson et al. (1988) *Proc. Natl. Acad. Sci. USA* 85:2444 using default parameters. Alternatively, it may be determined by the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277) (version 5.0.0 or later) (GCG program package (Devereux, J. et al., *Nucleic Acids Research* 12:387 (1984)), BLASTP, BLASTN, FASTA (Atschul, S. F. et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST or ClustalW of the National Center for Biotechnology Information.

The homology, similarity, or identity of polynucleotides or polypeptides may be determined by comparing sequence information using, for example, the GAP computer program, such as Needleman et al. (1970), *J Mol Biol.* 48:443 as disclosed in Smith and Waterman, *Adv. Appl. Math* (1981) 2:482. Briefly, the GAP program defines the homology, similarity, or identity as a value obtained by dividing the number of similarly aligned symbols (i.e., nucleotides or amino acids) by the total number of the symbols in the shorter of the two sequences. Default parameters for the GAP program may include (1) a binary comparison matrix (containing a value of 1 for identities and 0 for non-identities) and the weighted comparison matrix of Gribskov et al. (1986) *Nucl. Acids Res.* 14:6745, as disclosed in Schwartz and Dayhoff, eds., *Atlas Of Protein Sequence And Structure*, National Biomedical Research Foundation, pp. 353-358 (1979) (alternatively, a substitution matrix of EDNAFULL (EMBOSS version of NCBI NUC4.4); (2) a penalty of 3.0 for each gap and an additional 0.10 penalty for each symbol in each gap (or a gap opening penalty of 10 and a gap extension penalty of 0.5); and (3) no penalty for end gaps.

Further, the triple agonist of the present invention may have an increased in vivo half-life, as compared with any one of native GLP-1, native glucagon, and native GIP, but is not particularly limited thereto. For example, the triple agonist of the present invention may be in the form of a long-acting conjugate having an increased half-life by linking a biocompatible material (e.g., an immunoglobulin Fc region) for increasing the half-life to the triple agonist directly or via a linker, but is not limited thereto.

The triple agonist may be, but is not particularly limited to, a triple agonist which does not occur naturally.

The triple agonist of the present invention may include an intramolecular bridge (e.g., covalent crosslinking or non-covalent crosslinking), and specifically may be in the form of including a ring. For example, the triple agonist may be in the form where a ring is formed between amino acids at positions 12 and 16, and/or at positions 16 and 20 of the triple agonist, but it is not particularly limited thereto.

Non-limiting examples of the ring may include a lactam crosslinking (or a lactam ring).

Further, the triple agonist includes all of those which are modified to include an amino acid capable of forming a ring at the desired site so as to include a ring.

For example, the triple agonist may be a triple agonist, in which amino acid pairs at positions 12 and 16, or at positions 16 and 20 of the triple agonist may be replaced by glutamic acid or lysine capable of forming a ring, respectively, but is not limited thereto.

The ring may be formed between side chains of amino acids within the triple agonist, for example, in the form of a lactam ring formed between a side chain of lysine and a side chain of a glutamic acid, but is not particularly limited thereto.

Further, in the triple agonist of the present invention, a part of amino acids may be, but is not particularly limited to, substituted with another amino acid or a non-native compound to avoid the recognition by agonist degrading enzymes for increasing the in vivo half-life.

Specifically, the triple agonist of the present invention may be a peptide where the in vivo half-life may be increased by avoiding the recognition by the degrading enzymes via substitution of the 2nd amino acid sequence in the amino acid sequence of the triple agonist. However, any amino acid substitution or modification to avoid the recognition by in vivo degrading enzymes is included without limitation.

Further, the modification of the triple agonist of the present invention may include all of the modifications using L-type or D-type amino acids and/or non-natural amino acids; and/or a modification of native sequence, for example, a modification of a side chain functional group, an intramolecular covalent bonding, e.g., a ring formation between side chains, methylation, ubiquitination, phosphorylation, aminohexanation, biotinylation, etc.

Further, the modification may also include all of those where one or more amino acids are added to the amino and/or carboxy terminus.

During the substitution or addition of amino acids, not only 20 amino acids commonly found in human proteins, but also atypical amino acids or those which do not occur naturally may be used. Commercial sources of atypical amino acids may include Sigma-Aldrich, ChemPep Inc., and Genzyme Pharmaceuticals. The peptides including these amino acids and typical peptide sequences may be synthesized and purchased from commercial suppliers, e.g., American Peptide Company or Bachem (USA), or Anygen (Korea).

Amino acid derivatives may be obtained in the same manner, and for example, 4-imidazoacetic acid, etc. may be used.

Further, the triple agonist according to the present invention may be in the form of a variant where the N- and/or C-terminus thereof, etc. is chemically modified or protected by organic groups, or amino acids may be added to the terminus of the peptide, for its protection from proteases in vivo while increasing its stability.

Particularly, in the case of a chemically-synthesized peptide, N- and C-termini thereof are electrically charged, and therefore, in order to remove the electric charge, the N-terminus may be acetylated and/or the C-terminus may be amidated, but the triple agonist is not particularly limited thereto.

Specifically, the C-terminus of the triple agonist of the present invention may be amidated or may have a free carboxyl group (—COOH), or may not be modified, but is not limited thereto.

In one specific embodiment, the triple agonist may be amidated at the C-terminus thereof, but is not limited thereto.

In one specific embodiment, the triple agonist may be aglycosylated, but is not limited thereto.

The triple agonist according to the present invention may include all of the peptide as it is, salts thereof (e.g., pharmaceutically acceptable salts of the peptide), or solvates thereof. Further, the peptide may have any pharmaceutically acceptable form.

Types of the salts are not particularly limited. However, salts may be in a safe and effective form for individuals, for example, mammals, but are not particularly limited thereto.

The term "pharmaceutically acceptable" refers to a substance that may be effectively used for the intended use within the scope of a pharmaco-medical decision without inducing excessive toxicity, irritation, allergic responses, etc.

As used herein, the term "pharmaceutically acceptable salt" refers to a salt derived from a pharmaceutically acceptable inorganic acid, organic acid, or base. Examples of a suitable acid may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salt derived from a suitable base may include alkali metals such as sodium, potassium, etc., alkaline earth metals such as magnesium, etc., and ammonium, etc.

In addition, as used herein, the term "solvate" refers to a complex of the triple agonist according to the present invention or a salt thereof and a solvent molecule.

The triple agonist of the present invention may be synthesized by a solid-phase synthesis method, and may also be produced by a recombinant method, or may be prepared commercially, but is not limited thereto.

Further, the triple agonist of the present invention may be synthesized by a method well-known in the art, according to its length, e.g., by an automatic peptide synthesizer, and may also be produced by genetic engineering technology.

Specifically, the triple agonist of the present invention may be prepared by a standard synthesis method, a recombinant expression system, or any other method known in the art. Accordingly, the triple agonist of the present invention may be synthesized by many methods including, for example, the methods described below:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining a peptide by linking the peptide fragments, and then recovering the peptide.

These descriptions may also be applied to other specific embodiments or aspects of the present invention, but are not limited thereto.

Another aspect of the present invention provides a peptide conjugate having activities on glucagon receptor, GLP-1 receptor, and GIP receptor.

In the present invention, the peptide conjugate having activities on glucagon receptor, GLP-1 receptor, and GIP receptor may be in the form, in which a biocompatible material capable of increasing the in vivo half-life thereof is linked to the peptide having activities on glucagon receptor, GLP-1 receptor, and GIP receptor. In the present invention, the biocompatible material may be used interchangeably with a carrier.

In the present invention, the conjugate of the peptide may exhibit increased duration of the efficacy, as compared with the peptide to which the carrier is not linked, and in the present invention, such a conjugate is referred to as a "long-acting conjugate".

Meanwhile, the conjugate may be one which does not occur naturally.

In one specific embodiment of the present invention, the long-acting conjugate may be in the form, in which an immunoglobulin Fc region as a biocompatible material is linked to the triple agonist. Specifically, in the conjugate, the immunoglobulin Fc region is covalently linked to the triple agonist via a linker, but is not particularly limited thereto.

In one specific embodiment of the present invention, the conjugate may be a conjugate represented by the following Chemical Formula 1:

X-L-F [Chemical Formula 1]

wherein

X represents a peptide including any one sequence selected from the group consisting of SEQ ID NOS: 1 to 12;

L represents a linker including ethylene glycol repeating units;

F represents an immunoglobulin Fc region; and

"-" represents a covalent linkage.

In the long-acting conjugate of Chemical Formula 1, the linkage between X and F may be a physical or chemical bond, or a non-covalent or covalent bond, specifically a covalent bond, but is not limited thereto.

More specifically, X and L, and Land F may be linked to each other via a covalent bond. In this regard, the conjugate is a conjugate, in which X, L, and F are linked via covalent bonds, respectively, as in the order of Chemical Formula 1.

X of the long-acting conjugate of Chemical Formula 1 may be the above-described peptide (triple agonist) having activities on glucagon receptor, GLP-1 receptor, and GIP receptor, specifically a peptide including any one amino acid sequence of SEQ ID NOS: 1 to 12, or a peptide essentially consisting of or consisting of any one amino acid sequence of SEQ ID NOS: 1 to 12, but is not limited thereto.

In the present invention, the "peptide having activities on glucagon receptor, GLP-1 receptor, and GIP receptor" may be an element of one moiety constituting the conjugate, and specifically it may correspond to X in Chemical Formula 1 and may correspond to the triple agonist of the present invention. The triple agonist is the same as described above.

The long-acting conjugate of the present invention may exhibit significant activities on GLP-1 receptor, glucagon receptor, and GIP receptor, even in the form of the conjugate.

Specifically, the conjugate of the present invention may have 0.01% or more, 0.1% or more, 0.2% or more, 0.5% or more, 0.7% or more, 1% or more, 2% or more, 3% or more, 4% or more, 5% or more, 6% or more, 7% or more, 8% or more, 9% or more, 10% or more, 20% or more, 30% or more, 40% or more, 50% or more, 60% or more, 70% or more, 80% or more, 90% or more, 100% or more in vitro activity on GLP-1 receptor, glucagon receptor, and/or GIP receptor, as compared with the native thereof, but is not limited thereto.

With respect to the objects of the present invention, the triple agonist or the conjugate thereof may have 0.1% or more, 0.2% or more, 0.5% or more, 0.7% or more, 1% or more, 2% or more, 3% or more, 4% or more, 5% or more, 10% or more, 20% or more, 30% or more, 40% or more, 50% or more, 60% or more, 70% or more, 80% or more, 90% or more, 100% or more activity on GLP-1 receptor, glucagon receptor, and/or GIP receptor, as compared with the native thereof, but is not limited thereto.

The long-acting conjugate of Chemical Formula 1 may be in the form, in which the peptide (X) including any one amino acid sequence of SEQ ID NOS: 1 to 12 and a material capable of increasing the half-life thereof (F, e.g., an immunoglobulin Fc region) are linked to each other via a linker, wherein the conjugate may exhibit increased duration of efficacy, as compared with the peptide (X) including any one amino acid sequence of SEQ ID NOS: 1 to 12 which is not linked to the material capable of increasing the half-life (F, e.g., an immunoglobulin Fc region).

The long-acting conjugate of the present invention may be a conjugate, in which the triple agonist amidated at the C-terminus thereof and the immunoglobulin Fc region are linked to each other via a linker, but is not limited thereto.

The C-terminus of the peptide including the same sequence as any one sequence selected from SEQ ID NOS: 1 to 12 or a sequence including the same may be amidated or may have a free carboxyl group (—COOH), or may not be modified, but is not limited thereto.

In the conjugate, F is a material capable of increasing the half-life of X, i.e., the peptide or triple agonist having activities on glucagon receptor, GLP-1 receptor, and GIP receptor, and it corresponds to an element of one moiety constituting the conjugate of the present invention.

F and X may be linked to each other by a covalent bond, and F and X may be linked to each other via L by a covalent chemical bond.

The material capable of increasing the half-life of X may be a biocompatible material, for example, an FcRn-binding material, but is not particularly limited thereto.

For a more specific example, the FcRn-binding material may be an immunoglobulin Fc region, more specifically an IgG Fc region, or an aglycosylated IgG4 Fc region, but is not particularly limited thereto.

One or more amino acid side chains within the peptide of the present invention may be attached to the biocompatible material in order to increase in vivo solubility and/or half-life, and/or to increase bioavailability thereof. These modifications may reduce the clearance of therapeutic proteins and peptides.

The above-described biocompatible material may be soluble (amphipathic or hydrophilic) and/or non-toxic and/or pharmaceutically acceptable.

In one specific embodiment, in the long-acting conjugate of the present invention, the triple agonist and the immunoglobulin Fc region may be linked to each other, but is not limited thereto.

Specifically, in the long-acting conjugate of Chemical Formula 1, F may be an immunoglobulin Fc region, and more specifically the immunoglobulin Fc region may be derived from IgG, but is not particularly limited thereto.

In one specific embodiment of the present invention, F (immunoglobulin Fc region) is a dimer consisting of two polypeptide chains, and has a structure in which one end of L is linked to only one polypeptide chain of the two polypeptide chains, but is not limited thereto.

In the present invention, the "immunoglobulin Fc region" refers to a region including a heavy chain constant region 2(CH2) and/or a heavy chain constant region 3(CH3), excluding heavy chain and light chain variable regions of the immunoglobulin. The immunoglobulin Fc region may be an element constituting the moiety of the conjugate of the present invention. Specifically, the immunoglobulin Fc region corresponds to F in Chemical Formula 1.

As used herein, the Fc region encompasses not only a native sequence obtained from papain digestion of an immunoglobulin, but also derivatives thereof, for example, variants, in which one or more amino acid residues in the native sequence are converted by deletion, insertion, non-conservative or conservative substitution, or a combination thereof, and thus become different from the native sequence, etc. The above derivatives, substituents, and variants are required to retain FcRn-binding ability. In the present invention, F may be a human immunoglobulin region, but is not limited thereto. F (e.g., an immunoglobulin Fc region) has a structure, in which two polypeptide chains are linked to each other via a disulfide bond, only via a nitrogen atom of one chain of the two chains, but is not limited thereto. The linkage via the nitrogen atom may be linked via reductive amination to an epsilon amino group or the N-terminal amino group of lysine.

The reductive amination reaction refers to a reaction in which an amine group or an amino group of a reactant reacts with an aldehyde (i.e., a functional group capable of reductive amination) of another reactant to produce an amine, and then forms an amine bond by a reduction reaction. It is an organic synthesis reaction well known in the art.

In one specific embodiment of the long-acting conjugate of the triple agonist of the present invention, the immunoglobulin Fc region is linked to the linker via a nitrogen atom at the N-terminus thereof.

Such an immunoglobulin Fc region may include a hinge region in the heavy chain constant region, but is not limited thereto.

In the present invention, the immunoglobulin Fc region may include a specific hinge sequence at the N-terminus.

As used herein, the term "hinge sequence" refers to a region that is located in the heavy chain and forms a dimer of the immunoglobulin Fc region through a disulfide bond.

In the present invention, the hinge sequence may be altered to have only one cysteine residue by deleting a part in a hinge sequence having the following amino acid sequence, but is not limited thereto:

```
                                          (SEQ ID NO: 13)
Glu-Ser-Lys-Tyr-Gly-Pro-Pro-Cys-Pro-Ser-Cys-Pro.
```

The hinge sequence may include only one cysteine residue by deleting a cysteine residue at position 8 or 11 in the hinge sequence of SEQ ID NO: 13. The hinge sequence of the present invention may include only one cysteine residue and may consist of 3 to 12 amino acids, but is not limited thereto. More specifically, the hinge sequence of the present invention may have the following sequence: Glu-Ser-Lys-Tyr-Gly-Pro-Pro-Pro-Ser-Cys-Pro (SEQ ID NO: 14), Glu-Ser-Lys-Tyr-Gly-Pro-Pro-Cys-Pro-Ser-Pro (SEQ ID NO: 15), Glu-Ser-Lys-Tyr-Gly-Pro-Pro-Cys-Pro-Ser (SEQ ID NO: 16), Glu-Ser-Lys-Tyr-Gly-Pro-Pro-Cys-Pro-Pro (SEQ ID NO: 17), Lys-Tyr-Gly-Pro-Pro-Cys-Pro-Ser (SEQ ID NO: 18), Glu-Ser-Lys-Tyr-Gly-Pro-Pro-Cys (SEQ ID NO: 19), Glu-Lys-Tyr-Gly-Pro-Pro-Cys (SEQ ID NO: 20), Glu-Ser-Pro-Ser-Cys-Pro (SEQ ID NO: 21), Glu-Pro-Ser-Cys-Pro (SEQ ID NO: 22), Pro-Ser-Cys-Pro (SEQ ID NO: 23), Glu-Ser-Lys-Tyr-Gly-Pro-Pro-Ser-Cys-Pro (SEQ ID NO: 24), Lys-Tyr-Gly-Pro-Pro-Pro-Ser-Cys-Pro (SEQ ID NO: 25), Glu-Ser-Lys-Tyr-Gly-Pro-Ser-Cys-Pro (SEQ ID NO: 26), Glu-Ser-Lys-Tyr-Gly-Pro-Pro-Cys (SEQ ID NO: 27), Lys-Tyr-Gly-Pro-Pro-Cys-Pro (SEQ ID NO: 28), Glu-Ser-Lys-Pro-Ser-Cys-Pro (SEQ ID NO: 29), Glu-Ser-Pro-Ser-Cys-Pro (SEQ ID NO: 30), Glu-Pro-Ser-Cys (SEQ ID NO: 31), Ser-Cys-Pro (SEQ ID NO: 32).

More specifically, the hinge sequence may include an amino acid sequence of SEQ ID NO: 23 (Pro-Ser-Cys-Pro) or SEQ ID NO: 32 (Ser-Cys-Pro), but is not limited thereto.

In a more specific embodiment of the long-acting conjugate of the triple agonist of the present invention, in the conjugate, the N-terminus of the immunoglobulin Fc region is proline. In this conjugate, the Fc region is linked to the linker via a nitrogen atom of the proline.

In one embodiment of the long-acting conjugate of the triple agonist of the present invention, the immunoglobulin Fc region may have a dimer form in which two chains of the immunoglobulin Fc region form a homodimer or a heterodimer due to the presence of a hinge sequence. The conjugate of Chemical Formula 1 of the present invention may be in the form in which one end of the linker is linked to one chain of the immunoglobulin Fc region of the dimer, but is not limited thereto.

As used herein, the term "N-terminus" refers to the amino terminus of a protein or polypeptide, and includes the extreme end of the amino terminus or includes up to 1, 2, 3, 4, 5, 6, 7, 8, 9, or 10 or more amino acids from the extreme end. The immunoglobulin Fc region of the present invention may include a hinge sequence at the N-terminus, but is not limited thereto.

Further, the immunoglobulin Fc region of the present invention may be an extended Fc region including a part or the entirety of the heavy chain constant region 1 (CH1) and/or light chain constant region 1 (CL1), excluding the heavy chain and light chain variable regions of an immunoglobulin, as long as it has an effect substantially equivalent or improved, as compared to its native form. Further, the immunoglobulin Fc region may be a region in which a part of a significantly long amino acid sequence corresponding to CH2 and/or CH3 is removed.

For example, the immunoglobulin Fc region of the present invention may be 1) CH1 domain, CH2 domain, CH3 domain, and CH4 domain, 2) CH1 domain and CH2 domain, 3) CH1 domain and CH3 domain, 4) CH2 domain and CH3 domain, 5) a combination between one or two or more domains among CH1 domain, CH2 domain, CH3 domain and CH4 domain, and an immunoglobulin hinge region (or a part of the hinge region), and 6) a dimer between each domain of the heavy chain constant region and the light chain constant region, but is not limited thereto.

In the present invention, the immunoglobulin Fc region may be a dimer or multimer consisting of single-chain immunoglobulins consisting of domains of the same origin, but is not limited thereto.

Further, in one specific embodiment, the immunoglobulin Fc region F is a dimer consisting of two polypeptide chains, wherein the dimeric Fc region F and X may be covalently linked to each other via one identical linker L including ethylene glycol repeating units. In a specific embodiment, X is covalently linked to only one polypeptide chain of the two polypeptide chains of the dimeric Fc region F via the linker L. In a more specific embodiment, only one X molecule is covalently linked via L to one polypeptide chain, to which X is linked, of the two polypeptide chains of the dimeric Fc region F. In the most specific embodiment, F is a homodimer.

In another specific embodiment, the immunoglobulin Fc region F is a dimer consisting of two polypeptide chains, and one end of L is linked to only one polypeptide chain of the two polypeptide chains, but is not limited thereto.

In the long-acting conjugate of another embodiment of the present invention, it is also possible for two molecules of X to bind symmetrically to one Fc region in a dimeric form. In this regard, the immunoglobulin Fc region and X may be linked to each other via the linker (L), but are not limited to the above-described examples.

Further, the immunoglobulin Fc region of the present invention includes the native amino acid sequence as well as sequence derivatives thereof. The amino acid sequence derivative means that one or more amino acid residues in the natural amino acid sequence have a different sequence due to deletion, insertion, non-conservative or conservative substitution, or a combination thereof.

For example, amino acid residues at positions 214 to 238, 297 to 299, 318 to 322, or 327 to 331 in IgG Fc, which are known to be important for linkage, may be used as the sites suitable for variation.

Further, various types of derivatives are possible, for example, those where the site capable of forming a disulfide bond is removed, those where several N-terminal amino acids are removed from native Fc, those where a methionine residue is added to the N-terminus of native Fc, etc. Further, complement binding sites, e.g., C1q binding sites, or antibody-dependent cell-mediated cytotoxicity (ADCC) sites may be removed to remove the effector function. The techniques for preparing the sequence derivatives of the immunoglobulin Fc region are disclosed in International Publication Nos. WO 97/34631, WO 96/32478, etc.

Amino acid exchanges in a protein or peptide that do not alter the entire activity of a molecule are well known in the art (H. Neurath, R. L. Hill, *The Proteins*, Academic Press, New York, 1979). The most common exchanges occur between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly. In some cases, amino acids may be modified by phosphorylation, sulfation, acrylation, glycosylation, methylation, farnesylation, acetylation, amidation, etc.

The Fc derivatives described above may be those which exhibit the same biological activity as that of the Fc region of the present invention, and have increased structural stability of the Fc region against heat, pH, etc.

Further, such an Fc region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, the method of obtaining from a native form is a method of isolating whole immunoglobulins from human or animal organisms and then treating them with a protease. When treated with papain, the native form is digested into Fab and Fc, and when treated with pepsin, it is cleaved into pF'c and $F(ab)_2$. Fc or pF'c may be isolated using size exclusion chromatography, etc. In a more specific embodiment, the Fc region may be a recombinant immunoglobulin Fc region, in which a human-derived Fc region is obtained from a microorganism.

In addition, the immunoglobulin Fc region may have natural glycans or increased or decreased glycans compared to the natural type, or be in a deglycosylated form. The increase, decrease, or removal of glycans of the immunoglobulin Fc may be achieved by any methods commonly used in the art such as a chemical method, an enzymatic method, and a genetic engineering method using a microorganism. In this regard, the immunoglobulin Fc region obtained by removing glycans shows a significant decrease in binding affinity to a complement c1q and a decrease in or loss of antibody-dependent cytotoxicity or complement-dependent cytotoxicity, and thus unnecessary immune responses are not induced thereby in living organisms. Based thereon, a deglycosylated or aglycosylated immunoglobulin Fc region may be more suitable as a drug carrier in view of the objects of the present invention.

As used herein, the term "deglycosylation" refers to a Fc region from which glycan is removed using an enzyme and the term "aglycosylation" refers to a Fc region that is not glycosylated and produced in prokaryotes, more specifically *E. coli*.

Meanwhile, the immunoglobulin Fc region may be derived from humans or animals including cows, goats, pigs, mice, rabbits, hamsters, rats, guinea pigs, etc., and in a more specific embodiment, it may be derived from humans.

Further, the immunoglobulin Fc region may be an Fc region derived from IgG, IgA, IgD, IgE, IgM, or a combination or hybrid thereof. In a more specific embodiment, it may be derived from IgG or IgM, which are the most abundant proteins in human blood, and in an even more specific embodiment, it may be derived from IgG, which is known to enhance the half-lives of ligand binding proteins. In a more specific embodiment, the immunoglobulin Fc region may be an IgG4 Fc region, and in a most specific embodiment, the immunoglobulin Fc region may be an aglycosylated Fc region derived from a human IgG4, but is not limited thereto.

In addition, in a specific embodiment, the immunoglobulin Fc fragment may be a human IgG4 Fc fragment in the form of a homodimer in which two monomers are linked to each other via a disulfide bond (inter-chain) formed between cysteines that are amino acids located at position 3 of each monomer. In this regard, each monomer of the homodimer has or may have independent two inner disulfide bonds (intra-chain), i.e., a disulfide bond formed between cysteines at positions 35 and 95 and a disulfide bond formed between cysteines at positions 141 and 199.

Each monomer may consist of 221 amino acids and the number of amino acids constituting the homodimer may be 442 in total, without being limited thereto. Specifically, the immunoglobulin Fc fragment may be in the form of a homodimer in which two monomers each having an amino acid sequence of SEQ ID NO: 33 (consisting of 221 amino acids) are linked to each other via a disulfide bond between cysteines at position 3 of each monomer, wherein the monomers of the homodimer each independently have an intra-chain disulfide bond formed between cysteines at positions 35 and 95 and an intra-chain disulfide bond formed between cysteines at positions 141 and 199, without being limited thereto.

F of Chemical Formula 1 may include a monomer of the amino acid sequence of SEQ ID NO: 33, and F may be a homodimer of the monomer of the amino acid sequence of SEQ ID NO: 33, but is not limited thereto.

For example, the immunoglobulin Fc region may be a homodimer including an amino acid sequence of SEQ ID NO: 34 (consisting of 442 amino acids), but is not limited thereto.

In one specific embodiment, the immunoglobulin Fc region and X may not be glycosylated, but are not limited thereto.

Meanwhile, as used herein, the term "combination" means that polypeptides encoding single-chain immunoglobulin Fc regions of the same origin are linked to a single-chain polypeptide of a different origin to form a dimer or multimer. In other words, a dimer or a multimer may be prepared from two or more fragments selected from the group consisting of Fc regions of IgG Fc, IgA Fc, IgM Fc, IgD Fc, and IgE.

As used herein, the term "hybrid" means that sequences corresponding to two or more immunoglobulin Fc regions of different origins are present in a single-chain immunoglobulin constant region. In the present invention, various hybrid forms are possible. In other words, the hybrid domain may be composed of one to four domains selected from the group consisting of CH1, CH2, CH3, and CH4 of IgG Fc, IgM Fc, IgA Fc, IgE Fc, and IgD Fc, and may include a hinge region.

Meanwhile, IgG may be divided into the IgG1, IgG2, IgG3, and IgG4 subclasses, and the present invention may include combinations or hybrids thereof, specifically, the IgG2 and IgG4 subclasses, and most specifically, the Fc fragment of IgG4, which rarely has effector functions such as complement-dependent cytotoxicity (CDC).

Further, the above-described conjugate may have increased duration of efficacy, as compared with the native peptide, or as compared with X not modified with F, and such a conjugate may be not only in the above-described form but also in the form, in which it is encapsulated in biodegradable nanoparticles, but is not limited thereto.

In Chemical Formula 1, L is a non-peptidyl linker.

As used herein, the term "non-peptidyl linker" includes a biocompatible polymer in which two or more repeating units are conjugated. The repeating units are linked to each other through any covalent bond, not a peptide bond. The non-peptidyl linker may be an element constituting the moiety of the conjugate of the present invention, and corresponds to L in Chemical Formula 1.

The non-peptidyl linker applicable in the present invention may be used without limitation as long as it is a polymer resistant to proteolytic enzymes in vivo. In the present invention, the non-peptidyl linker may be used interchangeably with a non-peptidyl polymer.

Further, the non-peptidyl linker of the present invention binding to the polypeptide corresponding to F may be one type of polymer as well as a combination of different types of polymers.

In one specific embodiment, the conjugate may be a conjugate in which F and X are covalently linked together via the non-peptidyl linker, which includes, at both ends, reactive groups capable of binding to F, specifically, the immunoglobulin Fc region, and X, specifically, the triple agonist.

Specifically, in the present invention, the non-peptidyl linker may include reactive groups at ends thereof to form a conjugate through a reaction with other components constituting the conjugate. When the non-peptidyl linker having reactive functional groups at both ends bind to X and F of Chemical Formula 1 via respective reactive groups to form the conjugate, the non-peptidyl linker or non-peptidyl polymer may be referred to as a non-peptidyl polymer linker moiety or a non-peptidyl linker moiety.

Further, in one specific embodiment, the conjugate may be a conjugate in which F and X are covalently linked together via the non-peptidyl linker (L), which includes, at both ends, reactive groups capable of binding to F, specifically the immunoglobulin Fc region, and X, specifically a peptide drug.

The non-peptidyl linker may be, but is not particularly limited to, a linker including ethylene glycol repeating units, for example, polyethylene glycol. Derivatives thereof that are known in the art and derivatives that may be easily prepared by ordinary skill in the art are also included in the scope of the present invention.

As used herein, the "polyethylene glycol linker" includes a biocompatible polymer in which two or more ethylene glycol repeating units are bound. The repeating units are linked to each other through not a peptide bond but any covalent bond. The polyethylene glycol linker may be an element constituting the moiety of the conjugate of the present invention, and corresponds to L in Chemical Formula 1.

Specifically, L (polyethylene glycol linker) may be a linker including ethylene glycol repeating units, for example, polyethylene glycol, but is not limited thereto. As used herein, the polyethylene glycol is a term including all of an ethylene glycol homopolymer, a PEG copolymer, or a monomethyl-substituted PEG polymer (mPEG), but is not particularly limited thereto. Derivatives thereof that are known in the art and derivatives that may be easily prepared by ordinary skill in the art are also included in the scope of the present invention.

The polyethylene glycol linker may include the ethylene glycol repeating units while including, at the ends thereof, functional groups used in the preparation of a conjugate before being formed into the conjugate. In the long-acting conjugate according to the present invention, X and F may be linked to each other though the functional groups, but it is not limited thereto. In the present invention, the non-peptidyl linker may include two or three or more functional groups, wherein the respective functional groups are the same as or different from each other, but is not limited thereto.

Specifically, the linker may be polyethylene glycol (PEG) represented by the following Chemical Formula 2, but is not limited thereto:

[Chemical Formula 2]

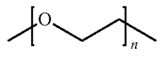

Here, n=10 to 2400, n=10 to 480, or n=50 to 250, but is not limited thereto.

In the long-acting conjugate, the PEG moiety may include a structure of $-(CH_2CH_2O)_n-$ and an oxygen atom interposed between the linking element and $-(CH_2CH_2O)_n-$, but is not limited thereto.

In one specific embodiment, the ethylene glycol repeating unit may be represented by, for example, $[OCH_2CH_2]_n$, wherein the value of n is a natural number and may be determined such that an average molecular weight, for example, a number average molecular weight of the $[OCH_2CH_2]_n$ site in the peptide conjugate is more than 0 kDa to about 100 kDa, but is not limited thereto. In another embodiment, the value of n is a natural number and may be determined such that an average molecular weight, for example, a number average molecular weight of the $[OCH_2CH_2]_n$ site in the peptide conjugate may be about 1 kDa to about 100 kDa, about 1 kDa to about 80 kDa, about 1 kDa to about 50 kDa, about 1 kDa to about 30 kDa, about 1 kDa to about 25 kDa, about 1 kDa to about 20 kDa, about 1 kDa to about 15 kDa, about 1 kDa to about 13 kDa, about 1 kDa to about 11 kDa, about 1 kDa to about 10 kDa, about 1 kDa to about 8 kDa, about 1 kDa to about 5 kDa, about 1 kDa to about 3.4 kDa, about 3 kDa to about 30 kDa, about 3 kDa to about 27 kDa, about 3 kDa to about 25 kDa, about 3 kDa to about 22 kDa, about 3 kDa to about 20 kDa, about 3 kDa to about 18 kDa, about 3 kDa to about 16 kDa, about 3 kDa to about 15 kDa, about 3 kDa to about 13 kDa, about 3 kDa to about 11 kDa, about 3 kDa to about 10 kDa, about 3 kDa to about 8 kDa, about 3 kDa to about 5 kDa, about 3 kDa to about 3.4 kDa, about 8 kDa to about 30 kDa, about 8 kDa to about 27 kDa, about 8 kDa to about 25 kDa, about 8 kDa to about 22 kDa, about 8 kDa to about 20 kDa, about 8 kDa to about 18 kDa, about 8 kDa to about 16 kDa, about 8 kDa to about 15 kDa, about 8 kDa to about 13 kDa, about 8 kDa to about 11 kDa, about 8 kDa to about 10 kDa, about 9 kDa to about 15 kDa, about 9 kDa to about 14 kDa, about 9 kDa to about 13 kDa, about 9 kDa to about 12 kDa, about 9 kDa to about 11 kDa, about 9.5 kDa to about 10.5 kDa, or about 10 kDa, but is not limited thereto.

Further, in one specific embodiment, the conjugate may have a structure in which the triple agonist (X) and the immunoglobulin Fc region (F) are covalently linked to each other via the linker (L) including ethylene glycol repeating units, but is not limited thereto.

Further, in one specific embodiment, the long-acting conjugate may have a structure in which the peptide (X) of the present invention and the immunoglobulin Fc region (F) are covalently linked to each other via the linker (L) including ethylene glycol repeating units, but is not limited thereto.

In another specific embodiment, in the long-acting conjugate, L may be the linker including ethylene glycol repeating units, and F may be a dimeric immunoglobulin Fc region. More specifically, one X molecule is covalently linked to one Fc region of the dimeric immunoglobulin Fc region via the linker including ethylene glycol repeating units, but is not limited thereto. In still another specific embodiment, one end of the linker including ethylene glycol repeating units may be linked to only one Fc region chain of two Fc region chains of the dimeric immunoglobulin Fc region, but is not limited thereto.

The non-peptidyl linker that may be used in the present invention may be used without limitation as long as it is a polymer resistant to proteolytic enzymes in vivo. Specifically, a molecular weight of the non-peptidyl polymer may be in the range of more than 0 kDa and about 200 kDa, specifically in the range of about 1 kDa to about 100 kDa, more specifically in the range of about 1 kDa to about 50 kDa, much more specifically in the range of about 1 kDa to 20 kDa, even much more specifically in the range of about 3.4 kDa to 10 kDa, and even much more specifically about 3.4 kDa, but is not limited thereto.

As used herein, the term "about" includes all of the ranges including ±0.5, ±0.4, ±0.3, ±0.2, ±0.1, etc., and includes all values in a range equal to or similar to the value following the term "about", but is not limited thereto.

Specifically, the non-peptidyl linker may have reactive groups at both ends thereof in a state where F and X are not bound thereto, and may bind with F and X via the reactive groups.

In one specific embodiment, both ends of the linker may bind to a thiol group, an amino group, or a hydroxyl group of the immunoglobulin Fc region and a thiol group, an amino group, an azide group, or a hydroxyl group of the peptide (X), but are not limited thereto.

Specifically, the linker may include, at both ends thereof, reactive groups capable of binding to the immunoglobulin Fc region and the peptide (X), respectively, specifically reactive groups capable of binding to a thiol group of cysteine; an amino group located at the N-terminus, lysine, arginine, glutamine, and/or histidine; and/or a hydroxyl group at the C-terminus of the immunoglobulin Fc region; and a thiol group of cysteine; an amino group of lysine, arginine, glutamine, and/or histidine; an azide group of azido-lysine; and/or a hydroxyl group of the peptide (X), but is not limited thereto.

More specifically, the reactive group of the linker may be one or more selected from the group consisting of an aldehyde group, a maleimide group, and a succinimide derivative, but is not limited thereto.

In the above, examples of the aldehyde group may include a propionaldehyde group, or a butyraldehyde group, but are not limited thereto.

In the above, examples of the succinimide derivative may include succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate, but are not limited thereto.

The linker may be linked to the immunoglobulin Fc region F and the peptide (triple agonist) X via the reactive groups to be converted into a linker moiety.

Further, a final product produced by reductive amination via aldehyde bonds is more stable than a linkage formed by an amide bond. The aldehyde reactive group selectively reacts with the N-terminus at low pH while forming a covalent bond with a lysine residue at high pH, e.g., at a pH of 9.0.

In addition, the reactive groups of both ends of the non-peptidyl linker may be the same as or different from each other, for example, aldehyde groups may be provided at both ends, and a maleimide group may be provided at one end and an aldehyde group, a propionaldehyde group, or a butyraldehyde group may be provided at the other end. However, the reactive groups are not particularly limited as long as F, specifically the immunoglobulin Fc region and X may be linked to the respective ends of the non-peptidyl linker.

For example, the non-peptidyl linker may include a maleimide group at one end and an aldehyde group, a propionaldehyde group, or a butyraldehyde group at the other end, as reactive groups.

When polyethylene glycol having hydroxyl reactive groups at both ends is used as the non-peptidyl polymer, the long-acting protein conjugate of the present invention may be prepared by activating the hydroxyl groups to various reactive groups by known chemical reactions, or using commercially available polyethylene glycol having modified reactive groups.

In a specific embodiment, the non-peptidyl polymer may be linked to a cysteine residue of X, more specifically a —SH group of cysteine, but is not limited thereto.

For example, the non-peptidyl polymer may be linked to a cysteine residue at position 10, a cysteine residue at position 24, or a cysteine residue at position 40 in the peptide corresponding to X, but is not particularly limited thereto. Specifically, the reactive group of the non-peptidyl polymer may be linked to the —SH group of the cysteine residue, and all of those described above will be applied to the reactive group.

Specifically, the reactive group of the non-peptidyl polymer may be linked to the —SH group of the cysteine residue, and all of those described above will be applied to the reactive group. When maleimide-PEG-aldehyde is used, the maleimide group may be linked to the —SH group of X via a thioether bond, and the aldehyde group may be linked to the —$NH_2$ group of F, specifically the immunoglobulin Fc via a reductive amination, but is not limited thereto. This is merely an example.

In another specific embodiment, the non-peptidyl polymer may be linked to the lysine residue of X, more specifically the amino group of the lysine, but is not limited thereto.

In addition, in the conjugate, the reactive group of the non-peptidyl polymer may be linked to —$NH_2$ located at the N-terminus of the immunoglobulin Fc region, but this is merely an example.

When maleimide-PEG-aldehyde is used, the maleimide group may be linked to the —SH group of the peptide via a thioether bond, and the aldehyde group may be linked to the —$NH_2$ group of the immunoglobulin Fc region via a reductive alkylation, but is not limited thereto. This is merely an example.

Through such reductive alkylation, the N-terminal amino group of the immunoglobulin Fc region is linked to the oxygen atom located at one end of the PEG through a linker functional group having a structure of —$CH_2CH_2CH_2$— to form a structure of -PEG-O—$CH_2CH_2CH_2NH$-immunoglobulin Fc. Through the thioether bond, a structure, in which one end of the PEG is linked to the sulfur atom located in the cysteine of the peptide, may be formed. The thioether bond described above may include a structure of

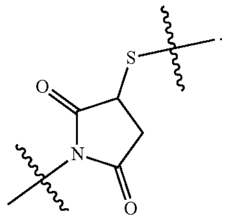 [SMILES: *SC1CC(=O)N(*)C1=O]

However, the present invention is not particularly limited to the above-described example, and this is merely an example.

Further, in the conjugate, the reactive group of the linker may be linked to —$NH_2$ located at the N-terminus of the immunoglobulin Fc region, but this is merely an example.

Further, in the conjugate, the peptide according to the present invention may be linked to the linker having reactive groups via the C-terminus, but this is merely an example.

As used herein, the term "C-terminus" refers to a carboxy terminus of the peptide, and with respect to the objects of the present invention, it refers to a site capable of binding with the linker. For example, the C-terminus may include all of an amino acid residue at the extreme end of the C-terminus and amino acid residues near the C-terminus, and specifically may include the $1^{st}$ to $20^{th}$ amino acid residues from the extreme end, but the C-terminus is not limited thereto.

Further, the above-described conjugate may have increased duration of efficacy, as compared with X not modified with F, and such a conjugate may be not only in the above-described form but also in a form, in which it is encapsulated in biodegradable nanoparticles.

Meanwhile, with regard to the above-described triple agonist and the long-acting conjugate thereof, the disclosures of International Publication Nos. WO 2017/116204 and WO 2017/116205 are incorporated by reference herein in its entirety.

Still another aspect of the present invention provides a polynucleotide encoding the peptide (triple agonist) or conjugate, a recombinant expression vector including the polynucleotide, and a transformant including the polynucleotide or the recombinant expression vector.

The peptide and conjugate are the same as described above.

Further, the isolated polynucleotide encoding the peptide or conjugate may include a polynucleotide sequence having 75% or more, specifically 85% or more, more specifically 90% or more, and much more specifically 95% or more sequence identity to the corresponding sequence in the scope of the present invention.

As used herein, the term "recombinant vector" refers to a DNA construct in which a target peptide, e.g., peptide is operably linked to an appropriate regulatory sequence to enable expression of the target peptide, e.g., peptide in an appropriate host.

The regulatory sequence includes a promoter capable of initiating transcription, any operator sequence for regulating such transcription, a sequence encoding a suitable mRNA ribosome binding site, and a sequence for regulating the termination of transcription and translation. The recombinant vector may be transformed into an appropriate host cell, and then may replicate or function regardless of a host genome or may be integrated into the genome itself.

The recombinant vector used in the present invention is not particularly limited, as long as it is replicable in a host cell, and may be prepared using any vector known in the art. Examples of vectors to be generally used may include native or recombinant plasmids, cosmids, viruses, and bacteriophages. The vector applicable in the present invention is not particularly limited, and any known expression vector may be used.

In order to produce the peptide or conjugate of the present invention, the recombinant vector is used to transform host cells. In addition, the transformed cell, which are part of the present invention, may be a cultured cell or cell line used for propagation of the nucleic acid fragment and the vector of the present invention or for recombinant production of the peptide or conjugate of the present invention.

As used herein, the "transformation" means introduction of a recombinant vector including a polynucleotide encoding a target protein into a host cell in such a way that the protein encoded by the polynucleotide is expressed in the host cell. As long as the transformed polynucleotide may be expressed in the host cell, it may be inserted into and located in the chromosome of the host cell or exist extrachromosomally, or it may be in any of the cases.

Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette may include a promoter operably linked to the polynucleotide, transcriptional termination signals, ribosome binding sites, and translation termination signals. The expression cassette may be in the form of a self-replicable expression vector. Additionally, the polynucleotide as it is may be introduced into the host cell and operably linked to sequences required for expression in the host cell, but is not limited thereto.

As used herein, the term "operably linked" means a functional linkage between a promoter sequence which initiates and mediates transcription of the polynucleotide encoding the peptide or conjugate of the present disclosure and the polynucleotide sequence.

The host suitable for the present invention is not particularly limited, as long as it allows expression of the polynucleotide of the present invention. Specific examples of the host applicable in the present invention may include bacteria of the genus *Escherichia* such as *E. coli*; bacteria of the genus *Bacillus* such as *Bacillus subtilis*; bacteria of the genus *Pseudomonas* such as *Pseudomonas putida*; yeasts such as *Pichia pastoris, Saccharomyces cerevisiae*, or *Schizosaccharomyces pombe*; insect cells such as *Spodoptera frugiperda* (Sf9); and animal cells such as CHO, COS, BSC, etc.

Still another aspect of the present invention provides a method of preparing the peptide or the conjugate.

The peptide and the conjugate are the same as described above.

The peptide of the present invention may be synthesized by a method well-known in the art, according to its length, e.g., by an automatic peptide synthesizer, and may also be produced by genetic engineering technology.

Specifically, the peptide of the present invention may be prepared by a standard synthesis method, a recombinant expression system, or any other method known in the art. Accordingly, the peptide of the present invention may be synthesized by many methods including, for example, the methods described below:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining a peptide by linking the peptide fragments, and then recovering the peptide.

For more specific example, a desired peptide may be produced, through genetic manipulation, by preparing a fusion gene encoding a fusion protein including a fusion partner and the peptide, transforming the fusion gene into a host cell, expressing the fusion gene in the form of a fusion protein, and cleaving and separating the peptide from the fusion protein using a protease or a compound. For this purpose, for example, an amino acid residue-encoding DNA sequence that may be cleaved by a protease such as Factor Xa or enterokinase, or a compound such as CNBr or hydroxylamine, may be inserted between the fusion partner and a polynucleotide encoding the peptide.

The conjugate of the present invention may be prepared by linking the peptide with the linker and the biocompatible material by simultaneous or sequential reaction. As long as the conjugate has the form, in which the peptide and the biocompatible material are linked via the linker, as a final product, the linkage sequence, method, reaction conditions, etc. are not particularly limited.

Still another aspect of the present invention provides a composition including the peptide or the conjugate.

The peptide and the conjugate are the same as described above.

The composition including the peptide or the long-acting conjugate of the present invention may be a composition for preventing or treating metabolic syndrome, specifically a pharmaceutical composition for preventing or treating metabolic syndrome. For example, the composition may be a pharmaceutical composition for preventing or treating metabolic syndrome including a pharmaceutically acceptable excipient; and a pharmaceutically effective amount of the peptide or the long-acting conjugate, but is not limited thereto.

As used herein, the term "pharmaceutically effective amount" may refer to a safe administration dose in which the peptide or the conjugate thereof exhibits a prophylactic or therapeutic effect on metabolic syndrome, but does not show toxicity or side effects to patients. Specifically, the pharmaceutically effective amount may refer to a dose capable of exhibit significant activities on GLP-1 receptor, glucagon receptor, and GIP receptor, but is not limited thereto.

In a specific embodiment of the present invention, the composition may be a pharmaceutical composition for preventing or treating metabolic syndrome, including a peptide including an amino acid sequence selected from the group consisting of SEQ ID NOS: 1 to 12 or a long-acting conjugate thereof, but is not limited thereto.

The "peptide" and "conjugate" are the same as described above.

As used herein, the term "preventing" refers to all kinds of actions associated with inhibition or delay of the onset of metabolic syndrome by administering the peptide, conjugate, or composition including the same, and the term "treating" refers to all kinds of actions associated with the improvement or advantageous changes in symptoms of metabolic syndrome by administering the peptide, conjugate, or composition including the same.

As used herein, the term "administering" refers to an introduction of a particular material to a patient by an appropriate manner. The composition may be, but is not particularly limited to, administered by a general route that enables the delivery of the composition to a target tissue in vivo, for example, intraperitoneal, intravenous, intramuscular, subcutaneous, intradermal, oral, topical, intranasal, intrapulmonary, and intrarectal administration.

As used herein, the term "metabolic syndrome" refers to symptoms, in which various diseases caused by chronic metabolic disorders occur alone or in combination. Particularly, diseases corresponding to metabolic syndrome may include impaired glucose tolerance, hypercholesterolemia, dyslipidemia, obesity, diabetes, hypertension, dyslipidemia-induced arteriosclerosis, atherosclerosis, arteriosclerosis, and coronary heart disease, etc., but are not limited thereto.

As used herein, the term "obesity" refers to excessive accumulation of adipose tissue in the body, and is defined as a body mass index (weight (kg) divided by height (m) squared) above 25. Obesity is usually caused by long-term energy imbalance between an excessive intake of nutrients and energy consumption. Obesity is a metabolic disease that affects the entire body, and increases the risk of diabetes and hyperlipidemia, and the risk of sexual dysfunction, arthritis, cardiovascular disease, and in some cases, is associated with cancer.

As used herein, the term "diabetes" is a type of metabolic disease such as lack of insulin secretion or abnormal function, and is characterized by hyperglycemia which occurs when the glucose levels in the blood elevates. Diabetes refers to a disease in which hyperglycemia causes various symptoms and signs, and causes the excretion of glucose into the urine. The diabetes of the present invention may include not only type 1 diabetes and type 2 diabetes, but also obesity-type diabetes, diabetes complications, and the like.

As used herein, the term "obesity-type diabetes" refers to diabetes with symptoms of obesity that cause diabetes, particularly, type 2 diabetes, or symptom of obesity in type 2 diabetes patients. About 80% to 90% of type 2 diabetes patients have symptoms of obesity, and these patients are characterized by insulin resistance. Proper exercise, diet, and drug therapy may prevent and alleviate obesity-type diabetes. In the present invention, the obesity-type diabetes may result from obesity.

As used herein, the term "diabetes complications" refers to various pathological symptoms occurring in the body when the blood glucose level remains high over a long period of time, and the diabetes complications are exemplified by retinopathy, renal dysfunction, neuropathy, stroke due to vascular disorders, kidney or heart disease or diabetic foot ulcer, and cardiovascular disease, but are not limited thereto. When the blood glucose level remains high over a long period of time, the risk of retinopathy, renal dysfunction, neuropathy, stroke due to vascular disorders, kidney or heart disease or diabetic foot ulcer, and cardiovascular disease increases. Therefore, effective blood glucose management is essential to prevent these complications.

As used herein, the term "dyslipidemia" refers to a state in which cholesterol and triglyceride levels are outside the normal range, and specifically refers to a state in which total cholesterol, LDL cholesterol, and triglycerides in the blood are elevated or HDL cholesterol is decreased.

The pharmaceutical composition of the present invention may further include a pharmaceutically acceptable carrier, excipient, or diluent. Such a pharmaceutically acceptable carrier, excipient, or diluent may be one which does not occur naturally.

As used herein, the term "pharmaceutically acceptable" refers to an amount sufficient to exhibit therapeutic effects without causing side-effects, and may be easily determined by those of ordinary skill in the art, based on factors well known in the medical field such as the type of disease, a patient's age, body weight, health status, gender, and sensitivity to drug, administration route, administration method, frequency of administration, duration of treatment, and a drug used in combination or concurrently.

The pharmaceutical composition including the triple agonist of the present invention may further include a pharmaceutically acceptable carrier. Although the carrier is not particularly limited, a binder, a lubricant, a disintegrator, an excipient, a solubilizer, a dispersant, a stabilizer, a suspending agent, a coloring agent, and a flavoring agent may be used for oral administration, a buffer, a preservative, an analgesic, a solubilizer, an isotonic agent, and a stabilizer may be used in combination for injectable preparations, and a base, an excipient, a lubricant, a preservative, etc. may be used for topical administration.

The composition of the present invention may be formulated into various forms in combination with the above-mentioned pharmaceutically acceptable carrier. For example, for oral administration, the composition may be formulated into tablets, troches, capsules, elixirs, suspensions, syrups, wafers, etc. For injectable preparations, the composition may be formulated into a single-dose ampoule or multidose form. The composition may also be formulated into solutions, suspensions, tablets, pills, capsules, sustained-release preparations, etc.

Meanwhile, examples of the carrier, excipient, and diluent suitable for formulation may include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, or mineral oils. Also, the composition may further include a filler, an anti-coagulant, a lubricant, a humectant, a flavoring agent, a preservative, etc.

In addition, the pharmaceutical composition of the present invention may have any one formulation selected from the group consisting of tablets, pills, powders, granules, capsules, suspensions, formulations for internal use, emulsions, syrups, sterilized aqueous solutions, non-aqueous solvents, lyophilized preparations, and suppositories.

Also, the composition may be formulated in a unit dosage form suitable for administration into a patient's body, specifically in a form useful for administration of protein medicines, according to a method commonly used in the art, and administered via an oral administration route or a parenteral administration route such as an intradermal, intravenous, intramuscular, intraarterial, intramedullary, intrathecal, intraventricular, intrapulmonary, transdermal, subcutaneous, intraperitoneal, intranasal, intestinal, topical, sublingual, vaginal, or rectal route using an administration method commonly used in the art, but is not limited thereto.

In addition, the triple agonist or the conjugate thereof may be used in combination with various carriers permitted as medicaments such as a saline solution or an organic solvent. As the medicaments, carbohydrates such as glucose, sucrose, or dextran, antioxidants such as ascorbic acid or glutathione, chelating agents, low-molecular-weight proteins, or other stabilizers may be used to improve stability or absorbability.

An administration dose and frequency of the pharmaceutical composition of the present invention may be determined depending on a type of a drug, as an active ingredient, together with various related factors such as a disease to be treated, administration route, a patient's age, gender, and body weight, and severity of the disease.

The total effective dose of the composition of the present invention may be administered to a patient in a single dose or may be administered for a long period of time in multiple doses according to a fractionated treatment protocol. In the pharmaceutical composition of the present invention, the content of the active ingredient may vary depending on the disease severity. Specifically, a preferred total daily dose of the conjugate of the present invention may be about 0.0001 mg to 500 mg per 1 kg of body weight of a patient. However, the effective dose of the conjugate is determined considering various factors including a patient's age, body weight, health conditions, gender, disease severity, diet, and excretion rate, in addition to administration route of the pharmaceutical composition and treatment frequency. In this regard, those skilled in the art may easily determine the effective dose suitable for the particular use of the composition of the present invention. The pharmaceutical composition according to the present invention is not particularly limited to the formulation and administration route and mode, as long as it shows the effects of the present invention.

The pharmaceutical composition of the present invention may have excellent in vivo duration and titer, thereby remarkably reducing the number and frequency of administration of the pharmaceutical preparation of the present invention.

Specifically, the triple agonist of the present invention, the long-acting conjugate thereof, or the composition including the same may be administered once a week, once every two weeks, once every four weeks, or once a month, but is not limited thereto.

Still another aspect of the present invention provides a method of preventing or treating metabolic syndrome, the method including the step of administering the peptide, or the conjugate of the peptide, or the composition including the same to an individual in need thereof.

The peptide or the composition including the same, the metabolic syndrome, preventing and treating are the same as described above.

In the present invention, the individual refers to an individual suspected of having metabolic syndrome, and the individual suspected of having metabolic syndrome refers to mammals such as humans, rats, livestock, etc. having metabolic syndrome or at risk of having metabolic syndrome, but any individual that may be treated with the peptide, the conjugate, or the composition including the same of the present invention may be included without limitation.

The method of the present invention may include administering a pharmaceutically effective amount of the pharmaceutical composition including the peptide. An appropriate Still another aspect of the present invention provides use of the peptide, the conjugate of the peptide, or the composition including the same for the prevention or treatment of metabolic syndrome.

Still another aspect of the present invention provides use of the peptide, the conjugate of the peptide, or the composition including the same in the preparation of a prophylactic or therapeutic agent for metabolic syndrome.

The peptide, the conjugate of the peptide, or the composition including the same, and the prevention and treatment of metabolic syndrome are the same as described above.

Hereinafter, the present invention will be described in more detail with reference to the following Examples. However, these Examples are for illustrative purposes only, and the scope of the present invention is not intended to be limited by these Examples.

Example 1: Preparation of Triple Agonist

Triple agonists exhibiting activities on all of GLP-1, GIP, and glucagon receptors were prepared, and sequences thereof are shown in Table 1 below.

TABLE 1

| SEQ ID NO | Sequence | Information |
|---|---|---|
| 1 | YXQGTFTSDYSKYLD**E**QRA**K**EFVQWLLDHHPSSGQPPPSC | Ring formation |
| 2 | YXQGTFTSDYSKYLD**E**QAA**K**EFVQWLLDHHPSSGQPPPSC | Ring formation |
| 3 | YXQGTFTSDYSKYLD**E**QRA**K**EFIAWLLDHHPSSGQPPPSC | Ring formation |
| 4 | YXQGTFTSDYSIYLD**E**QRA**K**EFIAWLLAHHPSSGQPPPSC | Ring formation |
| 5 | YXQGTFTSDYSKYLD**E**KRA**K**EFVQWLLDQHPSSGQPPPSC | Ring formation |
| 6 | YXQGTFTSDYSKALD**E**KAA**K**DFVQWLLDQHPSSGQPPPSC | Ring formation |
| 7 | YXQGTFTSDYSKALD**E**KAA**K**DFVQWLKDQHPSSGQPPPSC | Ring formation |
| 8 | YXQGTFTSDCSKYLD**E**KAA**K**EFVQWLLDHHPSSGQPPPS | Ring formation |
| 9 | YXEGTFTSDYS**E**YME**K**EAVREFICWLVKGGPSSGAPPPS | Ring formation |
| 10 | YXQGTFTSDYSKYLD**E**RAS**K**DFVQWLLDHHPSSGQPPPSC | Ring formation |
| 11 | YXQGTFTSDYSIYLD**E**KAA**K**EFVQWLLDQHPSSGQPPPSC | Ring formation |
| 12 | YXEGTFTSDYSIQLDKQAAXAFVQWLIAGGPSSGAPPPSK | |

total daily dose may be determined by a physician within the scope of correct medical decision, and may be administered once or divided into several doses. However, with respect to the objects of the present invention, it is preferable that a specific therapeutically effective amount for a particular patient will be applied depending on various factors including the type and extent of responses to be achieved, a specific composition, including whether other agents are used in some cases, a patient's age, body weight, general health conditions, gender and diet, administration time, an administration route and an excretion rate of the composition, duration of treatment, a drug used together with or concurrently with the specific composition, and similar factors well known in the medical field.

Specifically, the triple agonist of the present invention, the long-acting conjugate thereof, or the composition including the same may be administered once a week, once every two weeks, once every four weeks, or once a month, but is not limited thereto.

In the sequences described in Table 1, the amino acid indicated by X represents a non-native amino acid Aib (aminoisobutyric acid), and the underlined and bold amino acids mean that the underlined and bold amino acids form a lactam ring with each other. Meanwhile, the peptides were prepared by a solid-phase peptide synthesis method using a synthesizer. When a C-terminal amidated triple agonist was prepared by a solid-phase peptide synthesis method using a synthesizer, an amide resin was used for C-terminal amidation.

Example 2: Preparation of Long-Acting Conjugate of Triple Agonist

(1) Preparation Example 1 of Long-Acting Conjugate of Triple Agonist

For pegylation of 10 kDa PEG having a maleimide group and an aldehyde group at both ends respectively, i.e., maleimide-PEG-aldehyde (10 kDa, NOF, Japan) into a cysteine residue of each triple agonist of Example 1, each triple agonist and the maleimide-PEG-aldehyde were reacted at a molar ratio of 1:1 to 3 with a protein concentration of 1 mg/mL to 5 mg/mL at low temperature for 0.5 to 3 hours. In this case, the reaction was conducted in an environment including 50 mM Tris buffer (pH 7.5) to which 20% to 60% isopropanol was added. Upon completion of the reaction, the reaction solution was applied to SP sepharose HP (GE Healthcare, USA) to purify each triple agonist which was mono-pegylated on cysteine.

Next, the reaction was carried out at 4° C. to 8° C. for 12 to 18 hours, with a molar ratio of the purified mono-PEGylated triple agonist and an immunoglobulin Fc at a molar ratio of 1:1 to 5 and the protein concentration of 10 mg/ml to 50 mg/mL. The reaction was conducted in an environment in which a 10 mM to 50 mM sodium cyanoborohydride, as a reducing agent, and a 10% to 30% isopropanol were added to a 100 mM potassium phosphate buffer (pH 6.0). Upon completion of the reaction, each conjugate including the triple agonist and the immunoglobulin Fc was purified from the reaction solution by applying to a butyl sepharose FF purification column (GE Healthcare, USA) and a Source ISO purification column (GE Healthcare, USA).

With regard to the immunoglobulin region, two monomers, each having an amino acid sequence of SEQ ID NO: 33 (consisting of 221 amino acids), formed a homodimer via disulfide bonds between cysteine amino acids at position 3 of each monomer, wherein the monomers of the homodimer each independently formed intra-disulfide bonds between cysteines at positions 35 and 95, and intra-disulfide bonds between cysteines at positions 141 and 199.

After preparation, purity was 95% or more, as analyzed by reverse phase chromatography, size exclusion chromatography, and ion exchange chromatography.

(2) Preparation Example 2 of Long-Acting Conjugate of Triple Agonist

For PEGylation of 3.4 kDa or 10 kDa ALD (2) PEG (polyethylene glycol, wherein hydrogens at both ends are modified with propylaldehyde groups; NOF, Japan) into a lysine residue or the N-terminus of each triple agonist of Example 1, each triple agonist and PEG were reacted at a molar ratio of 1:5-1:20 with a protein concentration of 5 mg/mL to 10 mg/mL at 2° C. to 8° C. for 4 to 16 hours. In this case, the reaction was conducted in 20 mM HEPES (pH 7.5) and ethanol, and was performed by adding 20 mM sodium cyanoborohydride as a reducing agent. From the reaction solution, the mono-PEGylated triple agonist was purified by using a Source 15S column (GE, US) using a concentration gradient of potassium chloride and a buffer containing sodium citrate (pH 2.0) and ethanol.

The conjugate of the purified mono-PEGylated triple agonist and immunoglobulin Fc region was prepared and purified according to the same reaction and purification conditions as in Preparation Example 1.

Example 3: Measurement of In Vitro Activity of Triple Agonist

In order to measure the activities of the triple agonists prepared in Example 1, cell lines, each transformed with GLP-1 receptor, glucagon (GCG) receptor, or GIP receptor, were used to measure the cell activity in vitro.

Each cell line was transformed to express a human GLP-1 receptor, human glucagon receptor, or human GIP receptor gene in Chinese hamster ovary (CHO), and thus is suitable for measuring the activity of GLP-1, glucagon, or GIP. Therefore, the cell line transformed to have each receptor was used to measure activity on each receptor.

In order to measure the GLP-1, glucagon, and GIP activities of the triple agonists prepared in Example 1, human GLP-1, glucagon, GIP and the triple agonists prepared in Example 1 were subjected to a 4-fold serial dilution from 50 nM to 0.000048 nM. The CHO cells, in which the human GLP-1, glucagon, or GIP receptor was expressed, were each cultured in a 384-well plate for 24 hours. The culture medium was removed therefrom, and each of the serially diluted materials was added to the plate in an amount of 5 μL, respectively. Thereafter, 5 μL of a buffer containing a CAMP antibody was added, followed by incubation at room temperature for 15 minutes. Then, 10 μL of a detection mix containing a cell lysis buffer was added thereto to lyse the cells and reacted at room temperature for 90 minutes. The cell lysates, upon completion of the reaction, were applied to a LANCE CAMP kit (PerkinElmer, USA) to calculate the $EC_{50}$ value via accumulated CAMP, and the values were compared with one another. As a result, the activities thereof relative to those of human GLP-1, glucagon, and GIP are shown in Table 2. In Table 2, triple agonist peptides of SEQ ID NOS: 1 to 12, of which activities were confirmed, are C-terminal amidate triple agonists.

TABLE 2

Relative activity of triple agonist

| | In vitro activity relative to native peptide (%) | | |
|---|---|---|---|
| SEQ ID NO | vs. GLP-1 | vs. Glucagon | vs. GIP |
| 1 | 16.60 | 442.51 | 51.46 |
| 2 | 91.41 | 145.75 | 150.19 |
| 3 | 17.43 | 576.78 | 48.35 |
| 4 | 11.25 | 59.94 | 123.79 |
| 5 | 49.13 | 825.77 | 35.51 |
| 6 | 89.54 | 78.11 | 512.94 |
| 7 | 97.83 | 3.62 | 33.88 |
| 8 | 42.65 | 5.52 | 6.19 |
| 9 | 37.0 | 26.6 | 11.7 |
| 10 | 65.3 | 19.0 | 23.4 |
| 11 | 77.6 | 10.2 | 33.7 |
| 12 | 87.2 | 6.6 | 52.8 |

The peptides prepared above have the triple agonist function capable of activating all of GLP-1 receptor, GIP receptor, and glucagon receptor.

The above experimental results showed that the triple agonists of the present invention function as a triple agonist capable of activating all of glucagon, GLP-1, and GIP receptors, suggesting the potential thereof as therapeutic agents for metabolic syndrome.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds, are therefore intended to be embraced by the claims.

The invention claimed is:

1. A peptide having agonistic activity on a glucagon receptor, a glucagon-like peptide-1 (GLP-1) receptor, and a glucose-dependent insulinotropic polypeptide (GIP) receptor, wherein the peptide comprises any one sequence selected from the group consisting of SEQ ID NOS: 1 to 12.

2. The peptide of claim 1, wherein the peptide has 10% or more agonistic activity on a GLP-1 receptor, a glucagon receptor, and a GIP receptor, as compared with activities of native human GLP-1, glucagon, and GIP.

3. The peptide of claim 1, wherein the peptide has 70% or more agonistic activity on a GLP-1 receptor, a glucagon receptor, and a GIP receptor, as compared with agonistic activity of native human GLP-1, glucagon, and GIP.

4. The peptide of claim 1, wherein the peptide has 70% or more agonistic activity on a GLP-1 receptor, as compared with agonistic activity of native human GLP-1.

5. The peptide of claim 1, wherein the peptide has 70% or more agonistic activity on a glucagon receptor, as compared with agonistic activity of native human glucagon.

6. The peptide of claim 1, wherein the peptide has 70% or more agonistic activity on a GIP receptor, as compared with agonistic activity of native human GIP.

7. The peptide of claim 1, wherein the peptide has 100% or more agonistic activity on a glucagon receptor, as compared with agonistic activity of native glucagon while having 10% or more agonistic activity on both of a GLP-1 receptor and a GIP receptor, as compared with agonistic activity of native GLP-1 and GIP.

8. The peptide of claim 1, wherein the peptide has 100% or more agonistic activity on a GIP receptor, as compared with agonistic activity of native GIP while having 10% or more agonistic activity on both of a GLP-1 receptor and a glucagon receptor, as compared with agonistic of native GLP-1 and glucagon.

9. The peptide of claim 1, wherein an amino acid at position 12 and an amino acid at position 16, or an amino acid at position 16 and an amino acid at position 20 from the N-terminus form a lactam ring.

10. The peptide of claim 1, wherein the C-terminus of the peptide is amidated.

11. A long-acting conjugate represented by the following Chemical Formula 1:

X-L-F [Chemical Formula 1]

wherein X represents the peptide of claim 1;

L represents a linker including ethylene glycol repeating units,

F represents an immunoglobulin Fc region, and

- represents a covalent linkage between X and L and between L and F.

12. The long-acting conjugate of claim 11, wherein the immunoglobulin Fc region is an immunoglobulin Fc region derived from IgG, IgA, IgD, IgE, or IgM, or a combination thereof, or a hybrid thereof; wherein the immunoglobulin Fc region is an IgG4 Fc region; or wherein the immunoglobulin Fc region is aglycosylated.

13. The long-acting conjugate of claim 11, wherein a formula weight of the ethylene glycol repeating unit moiety in L is in the range of 1 kDa to 100 kDa.

14. The long-acting conjugate of claim 11, wherein L is polyethylene glycol.

15. The long-acting conjugate of claim 11, wherein F is a dimeric immunoglobulin Fc region.

16. The long-acting conjugate of claim 15, wherein one X molecule is covalently linked to one Fc region of the dimeric immunoglobulin Fc region via a linker including ethylene glycol repeating units; or wherein one end of the linker including ethylene glycol repeating units is linked to only one Fc region chain of the two Fc region chains of the dimeric immunoglobulin Fc region.

17. A method for treating metabolic syndrome, comprising administering a pharmaceutical composition to a patient in need thereof, wherein the pharmaceutical composition comprises the peptide of claim 1.

18. The method of claim 17, wherein the peptide is in the form of a long-acting conjugate, which is represented by the following Chemical Formula 1:

X-$L_a$-F [Chemical Formula 1]

wherein X represents a peptide having agonistic activity on a glucagon receptor, a glucagon-like peptide-1 (GLP-1) receptor, and a glucose-dependent insulinotropic polypeptide (GIP) receptor, wherein the peptide comprises any one sequence selected from the group consisting of SEQ ID NOS: 1 to 12;

L represents a linker including ethylene glycol repeating units,

F represents an immunoglobulin Fc region, and

- represents a covalent linkage between X and L and between L and F.

19. The method of claim 17, wherein the metabolic syndrome is one or more selected from the group consisting of impaired glucose tolerance, hypercholesterolemia, dyslipidemia, obesity, diabetes, hypertension, dyslipidemia-induced arteriosclerosis, atherosclerosis, arteriosclerosis, and coronary heart disease.

20. A polynucleotide encoding the peptide of claim 1.

* * * * *